(12) United States Patent
Ohsumi et al.

(10) Patent No.: US 7,256,209 B2
(45) Date of Patent: Aug. 14, 2007

(54) PYRAZOLE DERIVATIVES AND DIABETIC MEDICINE CONTAINING THEM

(75) Inventors: Koji Ohsumi, Kawasaki (JP); Takashi Umemura, Kawasaki (JP); Hiroyuki Matsueda, Kawasaki (JP); Toshihiro Hatanaka, Kawasaki (JP); Akiko Onuki, Kawasaki (JP); Katsumi Maezono, Kawasaki (JP); Yoko Kageyama, Kawasaki (JP); Nobuo Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/567,039

(22) Filed: Dec. 5, 2006

(65) Prior Publication Data

US 2007/0099979 A1 May 3, 2007

Related U.S. Application Data

(63) Continuation of application No. 11/255,937, filed on Oct. 24, 2005, which is a continuation of application No. 10/936,535, filed on Sep. 9, 2004, now Pat. No. 7,015,201, which is a continuation of application No. 10/427,959, filed on May 2, 2003, now Pat. No. 6,815,428, which is a continuation of application No. PCT/JP01/09555, filed on Oct. 31, 2001.

(30) Foreign Application Priority Data

Nov. 2, 2000 (JP) .............................. 2000-335851
Apr. 27, 2001 (JP) .............................. 2001-131264

(51) Int. Cl.
*A61K 31/415* (2006.01)
*C07D 231/12* (2006.01)

(52) U.S. Cl. ................................... 514/407; 548/373.1
(58) Field of Classification Search ............... 514/407; 548/373.1
See application file for complete search history.

(56) References Cited

U.S. PATENT DOCUMENTS

| 5,264,451 | A | 11/1993 | Kees |
| 5,274,111 | A | 12/1993 | Kees |
| 6,815,428 | B2 | 11/2004 | Ohsumi et al. |
| 6,908,905 | B2 * | 6/2005 | Ohsumi et al. ............... 514/25 |
| 2005/0043249 | A1 | 2/2005 | Ohsumi et al. |

FOREIGN PATENT DOCUMENTS

| EP | 0 850 946 | 7/1998 |
| EP | 1 213 296 | 6/2002 |
| JP | 2003-012686 | 1/2003 |
| WO | WO 01/16147 | 3/2001 |
| WO | WO 02/053573 | 7/2002 |
| WO | WO 02/068439 | 9/2002 |
| WO | WO 02/088157 | 11/2002 |

OTHER PUBLICATIONS

Kenneth L. Kees et al, "New Potent Antihyperglycemic Agents in db/db Mice: Synthesis and Structure-Activity Relationship Studies of (4-Substituted benzyl)(trifluoromethyl)pyrazoles and -pyrazolones", *J. Med. Chem.*, 1996, 39, pp. 3920-3928.

Kenji Tsujihara et al, "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", *J. Med. Chem.*, 1999, 42, pp. 5311-5324.

* cited by examiner

*Primary Examiner*—Kamal A. Saeed
(74) *Attorney, Agent, or Firm*—Oblon, Spivak, McClelland, Maier & Neustadt, P.C.

(57) ABSTRACT

The present invention provides pyrazole-O-glycoside derivatives represented by the following formulae, used as a diabetic medicine

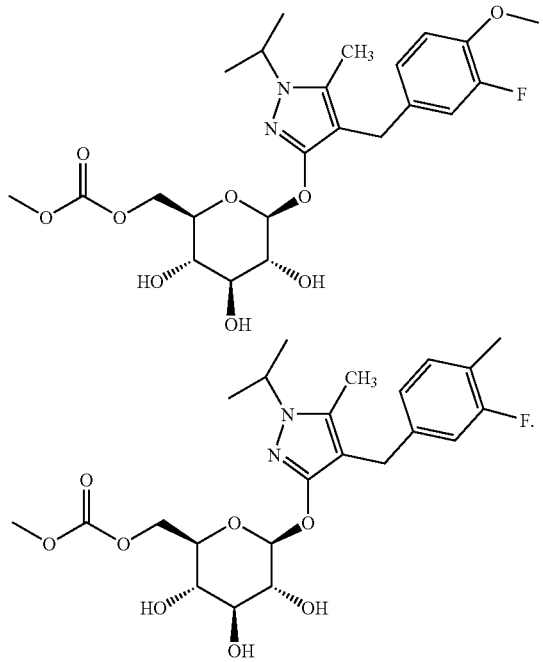

17 Claims, No Drawings

PYRAZOLE DERIVATIVES AND DIABETIC MEDICINE CONTAINING THEM

This application is a continuation of U.S. patent application Ser. No. 11/255,937 filed Oct. 24, 2005, now allowed, which is a continuation of U.S. patent application Ser. No. 10/936,535 filed Sep. 9, 2004, now U.S. Pat. No. 7,015,201, which is a continuation of U.S. patent application Ser. No. 10/427,959, filed May 2, 2003 now U.S. Pat. No. 6,815,428, which is a continuation of International Patent Application No. PCT/JP01/09555, filed on Oct. 31, 2001, and claims priority to Japanese Patent Application No. 2000-335851, filed on Nov. 2, 2000 and Japanese Patent Application No. 2001-13 1264, filed on Apr. 27, 2001, all of which are incorporated herein by reference in their entireties.

BACKGROUND OF THE INVENTION

The present invention relates to new pyrazole derivatives and diabetic medicine which have those compounds as an active ingredient.

$Na^+$-dependent glucose transporter (SGLT) is a membrane protein which transports glucose, and SGLT-1 and SGLT-2 are known. SGLT-2 mainly expresses in renal uriniferous tubules. Glucose that is filtered in glomeruli is reabsorbed at the renal uriferous tubules via SGLT, and the glucose taken is reused in the body through the bloodstream. When SGLT is inhibited, the amount of the glucose reabsorbed at renal uriniferous tubules lowers, and the glucose is discharged through urine. As a result, it is considered that the level of blood sugar decreases. At the present time, no medicine is clinically used such as that inhibiting reabsorption of glucose in the kidney.

DISCLOSURE OF THE INVENTION

The object of the present invention is to provide new pyrazole derivatives.

The object of the present invention is also to provide a pharmaceutical composition containing the new compounds.

The object of the present invention is also to provide a pharmaceutical composition for the treatment of diabetes which comprises the new compound.

The object of the present invention is to find and provide diabetic-medicine which is easy to synthesize, less toxic and has higher curative effect.

The present invention also intends to provide urinary sugar excretion inducers which have the new compounds.

Further, the present invention intends to provide the use of the new compounds for producing a pharmaceutical composition which reduces renal glucose reabsorption at renal uriniferous tubules.

The inventors have synthesized various derivatives (1A) or (1B) wherein glucose (namely, β-D-glucopyranose) or glucuronic acid (namely, β-D-glucopyranoside uronic acid) is bonded to pyrazole, and vigorously investigated the action of those derivatives on urinary sugar excretion. As the result of animal tests, they have found that the compounds of general formula (1A) or (1B) have the outstanding action on urinary sugar excretion and completed the present invention. These compounds have not ever been synthesized and, therefore, are completely new pyrazole-O-glycoside derivatives and pyrazole-O-glucuronide derivatives.

Namely, the present invention provides pyrazole derivatives of the following general formula (1A) or (1B) or pharmaceutically acceptable salts thereof:

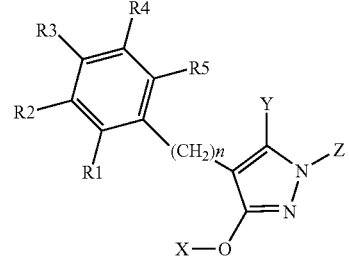

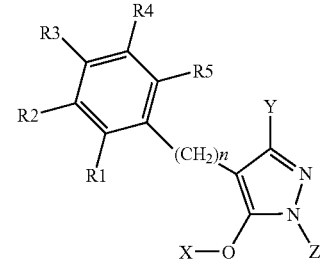

wherein X represents a β-D-glucopyranosyl group, of which one or more hydroxyl groups may be acylated or β-D-glucuronyl group, of which one or more hydroxyl groups may be acylated and carboxyl group may be esterified; Y represents a lower alkyl group or perfluoro lower alkyl group; Z represents a hydrogen atom, lower alkyl group, perfluoro lower alkyl group, aralkyl group or phenyl group; R1 to R5 may be the same or different and represent a hydrogen atom, lower alkyl group, perfluoro lower alkyl group, lower alkoxy group, perfluoro lower alkoxy group, lower alkylthio group, perfluoro lower alkylthio group, lower alkyl amino group, halogeno group, lower alkanoyl group, lower alkenyl group or lower alkynyl group, and n represents an integer from 0 to 3.

The present invention provides a pharmaceutical composition which comprises the above-mentioned pyrazole derivatives or pharmaceutically acceptable salts thereof as an active ingredient.

The present invention also provides a pharmaceutical composition for the treatment of diabetes which comprises the above-mentioned pyrazole derivatives or pharmaceutically acceptable salts thereof as an active ingredient.

The present invention also provides urinary sugar excretion inducers which comprise the above-mentioned pyrazole derivatives or pharmaceutically acceptable salts thereof as an active ingredient.

Further, the present invention provides the use of the above-mentioned pyrazole derivatives or pharmaceutically acceptable salts thereof for producing a pharmaceutical composition which reduces renal glucose reabsorption at renal uriniferons tobules.

BEST MODE FOR CARRYING OUT THE INVENTION

The term "lower" in the present specification indicates 1 to 6 carbon atoms, preferably 1 to 4 carbon atoms. The terms "alkyl", "alkenyl" and "alkynyl" in alkyl group, perfluoro lower alkyl group, lower alkoxy group, perfluoro lower alkoxy group, lower alkylthio group, perfluoro lower alkylthio group, lower alkyl amino group, lower alkanoyl group, lower alkenyl group or lower alkynyl group may be linear or branched.

An alkyl part in "aralkyl group" in the present specification is a lower alkyl group. An aryl part in "aralkyl group" is a monocyclic or bicyclic aromatic substituent having 5 to 12 carbon atoms.

Examples of the alkyl group include methyl group, ethyl group, propyl group, butyl group, pentyl group, isopropyl group, isobutyl group and isopentyl group. The perfluoro lower alkyl group is, for example, a trifluoromethyl group. Examples of the lower alkoxy group are methoxy group, ethoxy group, propyloxy group and isopropyloxy group. The perfluoro lower alkoxy group is, for example, a trifluoromethoxy group. The lower alkylthio group includes such as methylthio group, ethylthio group and propylthio group. The perfluoro lower alkylthio group is, for example, trifluoromethylthio group. The lower alkyl amino group includes such as methyl amino group, ethyl amino group, propyl amino group, dimethyl amino group and diethyl amino group. The lower alkanoyl group is, for example, acetyl group and propionyl group. The lower alkenyl group includes such as vinyl group, propenyl group and 2-methyl-1-propenyl group. The lower alkynyl group is, for example, ethynyl group and propynyl group. The aralkyl group includes such as benzyl group, benzyl group of which a benzene ring may have one or more substituents, phenethyl group and phenethyl group of which a benzene ring may have one or more substituents. The substituents of benzyl group and phenethyl group herein include lower alkoxy group, lower alkyl group, halogeno group and halogeno lower alkyl group. Examples of the halogeno group are fluorine atom, bromine atom, chlorine atom and iodine atom.

The groups for acylating hydroxyl group include acyl group and carbamate group; acyl group includes such as acetyl group, propionyl group, benzoyl group and pivaloyl group; carbamate group includes such as methyl carbonate group, ethyl carbonate group, propyl carbonate group, isopropyl carbonate group and phenyl carbonate group. The groups for esterifying carboxyl group include lower alkyl group such as methyl group, ethyl group, propyl group and isopropyl group.

In the above-mentioned general formula (1A) or (1B), one or more hydroxyl groups of β-D-glucopyranosyl group which is a group represented by X may be acylated. Especially, one or more hydroxyl groups of the said group may be acylated with the groups selected from alkanoyl groups having 2 to 20 carbon atoms, lower alkoxycarbonyl groups and benzoyl group. Examples of such groups are 6-O-acetyl-β-D-glucopyranosyl group and 6-O-methoxycarbonyl-β-D-glucopyranosyl group.

Further, one or more hydroxyl groups of β-D-glucuronyl group which is a group represented by X may be acylated and its carboxyl group may be esterified. Especially, one or more hydroxyl groups of the said group may be acylated with the groups selected from alkanoyl groups having 2 to 20 carbon atoms, lower alkoxycarbonyl groups and benzoyl group and its carboxylic acid may be esterified with lower alkyl group. An example of such groups is 6-O-methyl-β-D-glucuronyl group.

The groups represented by X are preferably β-D-glucopyranosyl group, 6-O-acetyl-β-D-glucopyranosyl group, 6-O-methoxycarbonyl-β-D-glucopyranosyl group, β-D-glucuronyl group and 6-O-methyl-β-D-glucuronyl group. Among them, β-D-glucopyranosyl group and β-D-glucuronyl group are more preferable. Particularly, the group represented by X is preferably β-D-glucopyranosyl group of which one or more hydroxyl groups may be acylated with the groups selected from alkanoyl groups having 2 to 20 carbon atoms, lower alkoxycarbonyl groups and benzoyl group. It is more preferable that the group is acylated with alkanoyl group having 2 to 6 carbon atoms or lower alkoxycarbonyl group. Among them, one hydroxyl group is preferably acylated. Most preferably, the hydroxyl group connected to a carbon atom at the 6th position is acylated. Examples of such groups represented by X are 6-O-acetyl-β-D-glucopyranosyl group and 6-O-methoxycarbonyl-β-D-glucopyranosyl group.

The groups represented by Y are preferably lower alkyl group having 1 to 3 carbon atoms or perfluoro lower alkyl group having 1 to 6 carbon atoms. A methyl group and trifluoromethyl group are particularly preferable.

The groups represented by Z are preferably hydrogen atom and lower alkyl group having 1 to 6 carbon atoms. A hydrogen atom, lower alkyl group having 1 to 3 carbon atoms, unsubstituted aralkyl group or aralkyl group of which all aryl part at the 4th position is substituted and unsubstituted phenyl group are also preferable. Further, hydrogen atom, methyl group, ethyl group, propyl group, isopropyl group, unsubstituted benzyl group or benzyl group of which an aryl part at the 4th position is substituted and unsubstituted phenyl group are more preferable. Among them, hydrogen atom, methyl group, ethyl group, propyl group and isopropyl group are more preferable, and isopropyl group is particularly preferable.

The groups represented by R1 to R5 are preferably lower alkyl group having 1 to 6 carbon atoms, lower alkylthio group having 1 to 6 carbon atoms, halogeno atom, lower alkoxy group, lower alkenyl group and lower alkynyl group. A methyl group, ethyl group, methylthio group, ethylthio group, fluorine atom, methoxy group, vinyl group, propenyl group, ethynyl group and propynyl group are more preferable. It is particularly preferable that one or two groups represented by R1 to R5 are one of the above-mentioned preferable groups and the rest of the groups are hydrogen atom. In this case, at least R3 is preferably one of the above-mentioned preferable groups. When two groups in R1 to R5 are one of the above-mentioned preferable groups, they may be the same or different from each other, but they are preferably different from each other. Further, when R3 is either lower alkyl group, lower alkoxy group, lower alkenyl group or lower alkynyl group, R4 or R5 is preferably a fluorine atom. It is preferable that one of R1, R2, R4 and R5 is halogeno group, or R1, R2, R4 and R5 are all hydrogen atom and R3 is lower alkyl group, lower alkoxy group, lower alkenyl group or lower alkynyl group. It is also preferable that one of R1, R2, R4 and R5 is a fluorine atom and R3 is methyl group, ethyl group, methoxy group, vinyl group or ethynyl group.

It is preferable that n represents an integer 1.

Y in general formula (1A) or (1B) is preferably trifluoromethyl group.

Further, it is preferable that in general formula (1A) or (1B), Y is trifluoromethyl group and n is 1.

It is also preferable that in general formula (1A) or (1B), Y is trifluoromethyl group, n is 1 and X is β-D-glucopyranosyl group, of which one or more hydroxyl groups may be acylated with the groups selected from alkanoyl group having 2 to 20 carbon atoms, lower alkoxycarbonyl group and benzoyl group.

It is also preferable that in general formula (1A) or (1B), Y is trifluoromethyl group, n is 1 and X is β-D-glucuronyl group, of which one or more hydroxyl groups may be acylated with the groups selected from alkanoyl group having 2 to 20 carbon atoms, lower alkoxycarbonyl group and benzoyl group and its carboxylic acid may be esterified with alkyl group.

It is also preferable that in general formula (1A) or (1B), Y is trifluoromethyl group, n is 1 and X is β-D-glucopyranosyl group.

It is also preferable that in general formula (1A) or (1B), Y is trifluoromethyl group, n is 1 and X is 6-acetyl-β-D-glucopyranosyl group.

It is also preferable that in general formula (1A) or (1B), Y is trifluoromethyl group, n is 1 and X is 6-carbomethoxy-β-D-glucopyranosyl group.

It is also preferable that in general formula (1A) or (1B), Y is trifluoromethyl group, n is 1 and X is β-D-glucuronyl group.

It is also preferable that in general formula (1A) or (1B), Y is trifluoromethyl group, n is 1 and X is 6-methyl-β-D-glucuronyl group.

It is also preferable that in general formula (1A) or (1B), X is β-D-glucopyranosyl group, of which one or more hydroxyl groups may be acylated with the groups selected from alkanoyl group having 2 to 20 carbon atoms, lower alkoxycarbonyl group and benzoyl group.

It is also preferable that in general formula (1A) or (1B), X is β-D-glucopyranosyl group, of which one or more hydroxyl groups may be acylated with lower alkoxycarbonyl group.

It is also preferable that in general formula (1A) or (1B), Y is lower alkyl group having 1 to 3 carbon atoms or perfluoro lower alkyl group having 1 to 6 carbon atoms; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is a hydrogen atom, lower alkyl group having 1 to 3 carbon atoms, unsubstituted aralkyl group or aralkyl group of which an aryl part at the 4th position is substituted or unsubstituted phenyl group; one of R1, R2, R4 and R5 is a halogeno group, or R1, R2, R4 and R5 are all hydrogen atom and R3 is a lower alkyl group, lower alkoxy group, halogeno group, lower alkenyl group or lower alkynyl group.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is a lower alkyl group and R4 or R5 is a fluorine atom.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is a lower alkoxy group and R4 or R5 is a fluorine atom.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is a lower alkynyl group.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is lower alkynyl group and R4 or R5 is a fluorine atom.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is a lower alkenyl group.

It is also preferable that in general formula (1A) or (1B), Y is a methyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is an isopropyl group; R3 is a lower alkenyl group and R4 or R5 is a fluorine atom.

It is also preferable that in general formula (1A) or (1B), Y is a methyl group or trifluoromethyl group; n is 1; X is β-D-glucopyranosyl group, of which one or more hydroxyl groups may be acylated with the groups selected from alkanoyl group having 2 to 20 carbon atoms, lower alkoxycarbonyl group and benzoyl group; Z is a hydrogen atom, isopropyl group, aralkyl group or phenyl group; one of R1, R2, R4 and R5 is a fluorine atom and R3 is a methyl group, ethyl group, methoxy group, vinyl group or ethynyl group.

The compounds or pharmaceutically acceptable salts thereof described below are also preferable:

4-((4-methylthiophenyl)methyl)-5-(trifluoromethyl)-1H-pyrazole-3-O-β-D-glucopyranoside;

4-((4-ethylthiophenyl)methyl)-5-(trifluoromethyl)-1H-pyrazole-3-O-β-D-glucopyranoside;

4-((4-propylthiophenyl)methyl)-5-(trifluoromethyl)-1H-pyrazole-3-O-β-D-glucopyranoside;

4-((4-isopropylthiophenyl)methyl)-5-(trifluoromethyl)-1H-pyrazole-3-O-β-D-glucopyranoside;

4-((4-methylphenyl)methyl)-5-(trifluoromethyl)-1H-pyrazole-3-O-β-D-glucopyranoside;

4-((4-ethylphenyl)methyl)-5-(trifluoromethyl)-1H-pyrazole-3-O-β-D-glucopyranoside;

4-((4-propylphenyl)methyl)-5-(trifluoromethyl)-1H-pyrazole-3-O-β-D-glucopyranoside;

4-((4-isopropylphenyl)methyl)-5-(trifluoromethyl)-1H-pyrazole-3-O-β-D-glucopyranoside;

4-((4-vinylphenyl)methyl)-5-(trifluoromethyl)-1H-pyrazole-3-O-β-D-glucopyranoside;

4-((4-ethylphenyl)methyl)-5-(trifluoromethyl)-1H-pyrazole-3-O-β-D-glucopyranoside;

4-((4-methylthiophenyl)ethyl)-5-(trifluoromethyl)-1H-pyrazole-3-O-β-D-glucopyranoside;

4-((4-ethylthiophenyl)ethyl)-5-(trifluoromethyl)-1H-pyrazole-3-O-β-D-glucopyranoside;

4-((4-propylthiophenyl)ethyl)-5-(trifluoromethyl)-1H-pyrazole-3-O-β-D-glucopyranoside;

4-((4-isopropylthiophenyl)ethyl)-5-(trifluoromethyl)-1H-pyrazole-3-O-β-D-glucopyranoside;

4-((3-methylthiophenyl)ethyl)-5-(trifluoromethyl)-1H-pyrazole-3-O-β-D-glucopyranoside;

4-((3-ethylthiophenyl)ethyl)-5-(trifluoromethyl)-1H-pyrazole-3-O-β-D-glucopyranoside;

4-((3-propylthiophenyl)ethyl)-5-(trifluoromethyl)-1H-pyrazole-3-O-β-D-glucopyranoside;

4-((3-isopropylthiophenyl)ethyl)-5-(trifluoromethyl)-1H-pyrazole-3-O-β-D-glucopyranoside;

4'-((4'-methylthiophenyl)methyl)-5'-trifluoromethyl-3'-O-(6-0-carbomethoxy-β-D-glucopyranosyl)-1H-pyrazole;

4'-((4'-ethylphenyl)methyl)-5'-(trifluoromethyl)-3'-O-(6-0-carbomethoxy-β-D-glucopyranosyl)-1H-pyrazole;

4'-((4'-methylthiophenyl)methyl)-5'-trifluoromethyl-3'-O-(2,3,4,6-0-tetraacetyl-β-D-glucopyranosyl)-1H-pyrazole;

4'-((4'-ethylphenyl)methyl)-5'-(trifluoromethyl)-3'-O-(2,3,4,6-0-tetraacetyl-β-D-glucopyranosyl)-1H-pyrazole;

4-[(4-trifluoromethoxyphenyl)methyl]-5-trifluoromethyl-1H-pyrazole-3-O-β-D-glucopyranoside;

4'-[(4'-trifluoromethoxyphenyl)methyl]-5'-trifluoromethyl-1H-pyrazole-3'-O-(2,3,4,6-0-tetraacetyl)-β-D-glucopyranoside;

4'-[(4'-trifluoromethoxyphenyl)methyl]-5'-trifluoromethyl-1H-pyrazole-3'-O-(6-carbomethoxy)-β-D-glucopyranoside;
4-[(4-ethylphenyl)methyl]-1-benzyl-5-trifluoromethyl-1H-pyrazole-3-O-β-D-glucopyranoside;
4'-[(4-ethylphenyl)methyl]-1'-benzyl-5'-trifluoromethyl-1H-pyrazole-3'-O-(2,3,4,6-tetraacetyl)-β-D-glucopyranoside;
4'-[(4-ethylphenyl)methyl]-1'-benzyl-5'-trifluoromethyl-1H-pyrazole-3'-O-(6-carbomethoxy)-β-D-glucopyranoside;
4-[(4-ethylphenyl)methyl]-1-[(4-methoxyphenyl)methyl]-5-trifluoromethyl-1H-pyrazole-3-O-β-D-glucopyranoside;
4'-[(4-ethylphenyl)methyl]-1'-[(4-methoxyphenyl)methyl]-5'-trifluoromethyl-1H-pyrazole-3'-O-(2,3,4,6-tetraacetyl)-β-D-glucopyranoside;
4'-[(4-ethylphenyl)methyl]-1'-[(4-methoxyphenyl)methyl]-5'-trifluoromethyl-1H-pyrazole-3'-O-(6-carbomethoxy)-β-D-glucopyranoside;
4-[(4-ethylphenyl)methyl]-1-phenyl-5-trifluoromethyl-1H-pyrazole-3-O-β-D-glucopyranoside;
4'-[(4-ethylphenyl)methyl]-1'-phenyl-5'-trifluoromethyl-1H-pyrazole-3'-O-(2,3,4,6-tetraacetyl)-β-D-glucopyranoside;
4'-[(4-ethylphenyl)methyl]-1'-phenyl-5'-trifluoromethyl-1H-pyrazole-3'-O-(6-carbomethoxy)-β-D-glucopyranoside;
4'-((3-fluoro-4-methoxyphenyl)methyl)-1'-isopropyl-5'-methyl-1H-pyrazole-3'-O-(6-carbomethoxy)-β-D-glucopyranoside;
4'-((3-fluoro-4-methylphenyl)methyl)-1'-isopropyl-5'-methyl-1H-pyrazole-3'-O-(6-carbomethoxy)-β-D-glucopyranoside;
4'-((2-fluoro-4-methoxyphenyl)methyl)-1'-isopropyl-5'-methyl-1H-pyrazole-3'-O-(6-carbomethoxy)-β-D-glucopyranoside;
4'-((2-fluoro-4-methylphenyl)methyl)-1'-isopropyl-5'-methyl-1H-pyrazole-3'-O-(6-carbomethoxy)-β-D-glucopyranoside;
4'-((2-fluoro-4-ethylphenyl)methyl)-1'-isopropyl-5'-methyl-1H-pyrazole-3'-O-(6-carbomethoxy)-β-D-glucopyranoside;
4'-((3-fluoro-4-ethylphenyl)methyl)-1'-isopropyl-5'-methyl-1H-pyrazole-3'-O-(6-carbomethoxy)-β-D-glucopyranoside;
4'-((4-ethynylphenyl)methyl)-1'-isopropyl-5'-methyl-1H-pyrazole-3'-O-(6-carbomethoxy)-β-D-glucopyranoside;
4'-((2-fluoro-4-ethynylphenyl)methyl)-1'-isopropyl-5'-methyl-1H-pyrazole-3'-O-(6-carbomethoxy)-β-D-glucopyranoside;
4'-((3-fluoro-4-ethynylphenyl)methyl)-1'-isopropyl-5'-methyl-1H-pyrazole-3'-O-(6-carbomethoxy)-β-D-glucopyranoside;
4'-((4-(1-propynyl)phenyl)methyl)-1'-isopropyl-5'-methyl-1H-pyrazole-3'-O-(6-carbomethoxy)-β-D-glucopyranoside;
4'-((3-fluoro-4-(1-propynyl)phenyl)methyl)-1'-isopropyl-5'-methyl-1H-pyrazole-3'-O-(6-carbomethoxy)-β-D-glucopyranoside;
4'-((2-fluoro-4-(1-propynyl)phenyl)methyl)-1'-isopropyl-5'-methyl-1H-pyrazole-3'-O-(6-carbomethoxy)-β-D-glucopyranoside;
4-((3-fluoro-4-methoxyphenyl)methyl)-1-isopropyl-5-methyl-1H-pyrazole-3-O-β-D-glucopyranoside;
4-((3-fluoro-4-methylphenyl)methyl)-1-isopropyl-5-methyl-1H-pyrazole-3-O-β-D-glucopyranoside;
4-((2-fluoro-4-methoxyphenyl)methyl)-1-isopropyl-5-methyl-1H-pyrazole-3-O-β-D-glucopyranoside;
4-((2-fluoro-4-methylphenyl)methyl)-1-isopropyl-5-methyl-1H-pyrazole-3-O-β-D-glucopyranoside;
4-((2-fluoro-4-ethylphenyl)methyl)-1-isopropyl-5-methyl-1H-pyrazole-3-O-β-D-glucopyranoside;
4-((3-fluoro-4-ethylphenyl)methyl)-1-isopropyl-5-methyl-1H-pyrazole-3-O-β-D-glucopyranoside;
4-((4-ethynylphenyl)methyl)-1-isopropyl-5-methyl-1H-pyrazole-3-O-β-D-glucopyranoside;
4-((2-fluoro-4-ethynylphenyl)methyl)-1-isopropyl-5-methyl-1H-pyrazole-3-O-β-D-glucopyranoside;
4-((3-fluoro-4-ethynylphenyl)methyl)-1-isopropyl-5-methyl-1H-pyrazole-3-O-β-D-glucopyranoside;
4-((4-(1-propynyl)phenyl)methyl)-1-isopropyl-5-methyl-1H-pyrazole-3-O-β-D-glucopyranoside;
4-((3-fluoro-4-(1-propynyl)phenyl)methyl)-1-isopropyl-5-methyl-1H-pyrazole-3-O-β-D-glucopyranoside;
4-((2-fluoro-4-(1-propynyl)phenyl)methyl)-1-isopropyl-5-methyl-1H-pyrazole-3-O-β-D-glucopyranoside;
4-((4-methylthiophenyl)methyl)-5-(trifluoromethyl)-1H-pyrazole-3-yl-β-D-glucopyranoside uronic acid;
4-((4-ethylthiophenyl)methyl)-5-(trifluoromethyl)-1H-pyrazole-3-yl-β-D-glucopyranoside uronic acid;
4-((4-propylthiophenyl)methyl)-5-(trifluoromethyl)-1H-pyrazole-3-yl-β-D-glucopyranoside uronic acid;
4-((4-isopropylthiophenyl)methyl)-5-(trifluoromethyl)-1H-pyrazole-3-yl-β-D-glucopyranoside uronic acid;
4-((4-methylphenyl)methyl)-5-(trifluoromethyl)-1H-pyrazole-3-yl-β-D-glucopyranoside uronic acid;
4-((4-ethylphenyl)methyl)-5-(trifluoromethyl)-1H-pyrazole-3-yl-β-D-glucopyranoside uronic acid;
4-((4-propylphenyl)methyl)-5-(trifluoromethyl)-1H-pyrazole-3-yl-β-D-glucopyranoside uronic acid;
4-((4-isopropylphenyl)methyl)-5-(trifluoromethyl)-1H-pyrazole-3-yl-β-D-glucopyranoside uronic acid;
4-((4-vinylphenyl)methyl)-5-(trifluoromethyl)-1H-pyrazole-3-yl-β-D-glucopyranoside uronic acid;
4-((4-ethynylphenyl)methyl)-5-(trifluoromethyl)-1H-pyrazole-3-yl-β-D-glucopyranoside uronic acid;
4-((4-methylthiophenyl)ethyl)-5-(trifluoromethyl)-1H-pyrazole-3-yl-β-D-glucopyranoside uronic acid;
4-((4-ethylthiophenyl)ethyl)-5-(trifluoromethyl)-1H-pyrazole-3-yl-β-D-glucopyranoside uronic acid;
4-((4-propylthiophenyl)ethyl)-5-(trifluoromethyl)-1H-pyrazole-3-yl-β-D-glucopyranoside uronic acid;
4-((4-isopropylthiophenyl)ethyl)-5-(trifluoromethyl)-1H-pyrazole-3-yl-β-D-glucopyranoside uronic acid;
4-((3-methylthiophenyl)ethyl)-5-(trifluoromethyl)-1H-pyrazole-3-yl-β-D-glucopyranoside uronic acid;
4-((3-ethylthiophenyl)ethyl)-5-(trifluoromethyl)-1H-pyrazole-3-yl-β-D-glucopyranoside uronic acid;
4-((3-propylthiophenyl)ethyl)-5-(trifluoromethyl)-1H-pyrazole-3-yl-β-D-glucopyranoside uronic acid;
4-((3-isopropylthiophenyl)ethyl)-5-(trifluoromethyl)-1H-pyrazole-3-yl-β-D-glucopyranoside uronic acid;
methyl 4-((4-methylthiophenyl)methyl)-5-(trifluoromethyl)-1H-pyrazole-3-yl-β-D-glucopyranouronate; and
ethyl 4-((4-methylthiophenyl)methyl)-5-(trifluoromethyl)-1H-pyrazole-3-yl-β-D-glucopyranouronate.

Among the above-mentioned examples, the following compounds or pharmaceutically acceptable salts thereof are particularly preferable:

4-((4-methylthiophenyl)methyl)-5-(trifluoromethyl)-1H-pyrazole-3-O-β-D-glucopyranoside;
4-((4-ethylphenyl)methyl)-5-(trifluoromethyl)-1H-pyrazole-3-yl-β-D-glucopyranoside uronic acid;
4-[(4-ethylphenyl)methyl]-1-benzyl-5-trifluoromethyl-1H-pyrazole-3-O-β-D-glucopyranoside;
4'-[(4'-ethylphenyl)methyl]-1'-benzyl-5'-trifluoromethyl-1H-pyrazole-3'-O-(6-carbomethoxy)-β-D-glucopyranoside;
4-[(4-ethylphenyl)methyl]-1-[(4-methoxyphenyl)methyl]-5-trifluoromethyl-1H-pyrazole-3-O-β-D-glucopyranoside;

4'-[(4-ethylphenyl)methyl]-1'-[(4'-methoxyphenyl)methyl]-5'-trifluoromethyl-1H-pyrazole-3'-O-(6-carbomethoxy)-β-D-glucopyranoside;
4-[(4-ethylphenyl)methyl]-1-phenyl-5-trifluoromethyl-1H-pyrazole-3-O-β-D-glucopyranoside;
4'-[(4'-ethylphenyl)methyl]-1'-phenyl-5'-trifluoromethyl-1H-pyrazole-3'-O-(6-carbomethoxy)-β-D-glucopyranoside;
4-[(3-fluoro-4-methoxyphenyl)methyl]-1-isopropyl-5-methyl-1H-pyrazole-3-O-β-D-glucopyranoside;
4'-[(3'-fluoro-4'-methoxyphenyl)methyl]-1'-isopropyl-5'-methyl-1H-pyrazole-3'-O-(6-carbomethoxy)-β-D-glucopyranoside;
4-[(2-fluoro-4-methoxyphenyl)methyl]-1-isopropyl-5-methyl-1H-pyrazole-3-O-β-D-glucopyranoside;
4'-[(2-fluoro-4-methoxyphenyl)methyl]-1'-isopropyl-5'-methyl-1H-pyrazole-3'-O-(6-carbomethoxy)-β-D-glucopyranoside;
4-[(3-fluoro-4-methylphenyl)methyl]-1-isopropyl-5-methyl-1H-pyrazole-3-O-β-D-glucopyranoside; and
4'-[(3'-fluoro-4'-methylphenyl)methyl]-1'-isopropyl-5'-methyl-1H-pyrazole-3'-O-(6-carbomethoxy)-β-D-glucopyranoside.

Among the above-mentioned examples, the following compounds or pharmaceutically acceptable salts thereof are particularly preferable:

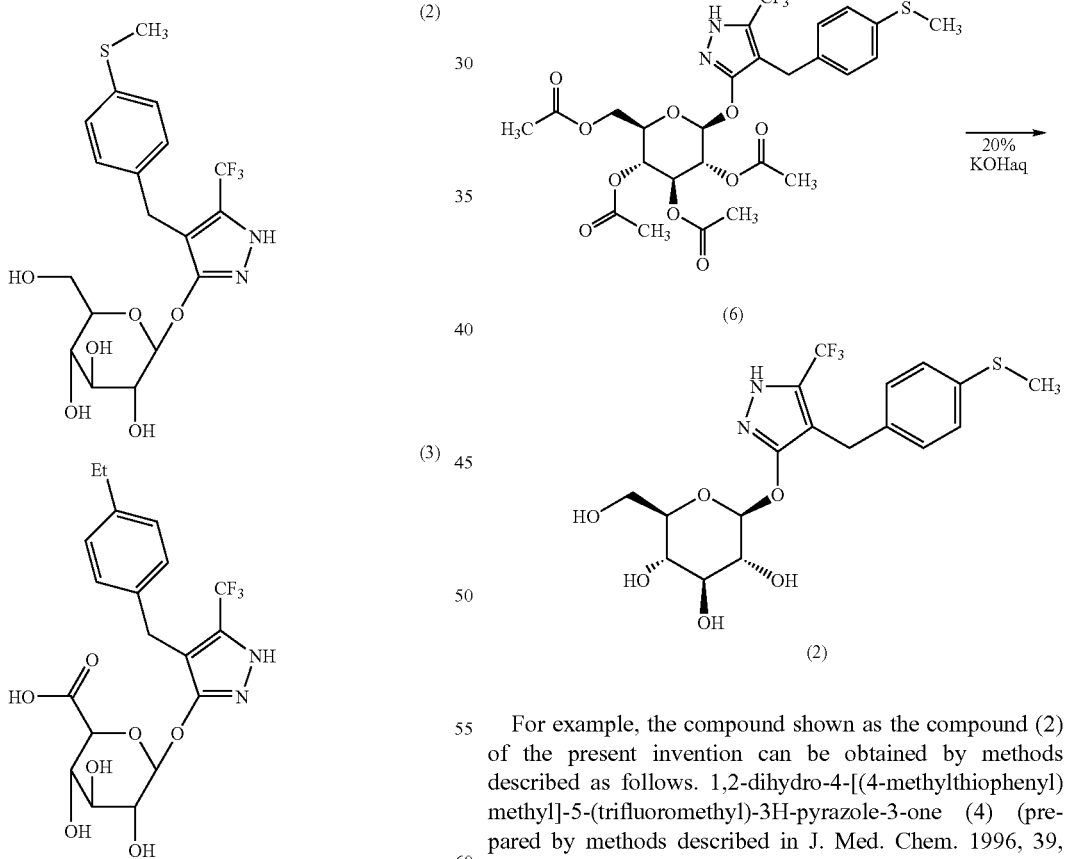

The following compounds or pharmaceutically acceptable salts thereof are also preferable:
4'-[(4-ethylphenyl)methyl]-1'-isopropyl-5'-methyl-1H-pyrazole-3'-O-(6-carbomethoxy)-β-D-glucopyranoside; and
4-[(4-ethylphenyl)methyl]-1-isopropyl-5'-methyl-1H-pyrazole-3-O-β-D-glucopyranoside.

As methods for producing pyrazole derivatives (1A) or (1B) in the present invention, for example, the compounds are produced in accordance with methods described below when X is β-D-glucopyranosyl group or β-D-glucuronyl group.

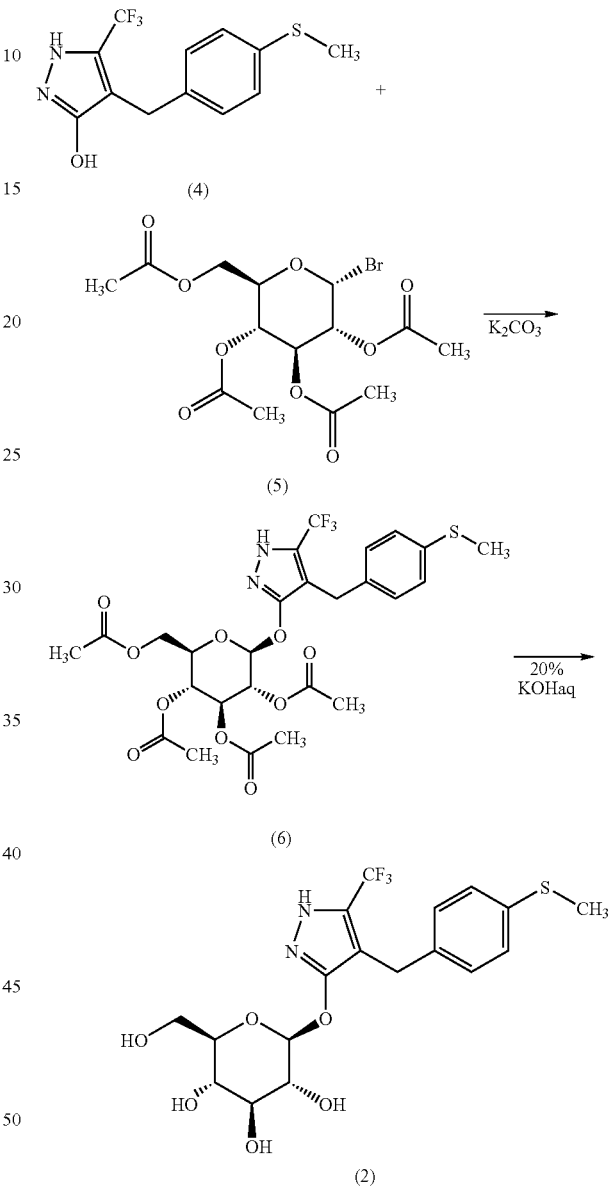

For example, the compound shown as the compound (2) of the present invention can be obtained by methods described as follows. 1,2-dihydro-4-[(4-methylthiophenyl)methyl]-5-(trifluoromethyl)-3H-pyrazole-3-one (4) (prepared by methods described in J. Med. Chem. 1996, 39, 3920-3928) is reacted with 2,3,4,6-tetra-O-acetyl-α-D-glucopyranosyl bromide in the presence of potassium carbonate in chloroform-water overnight. The product is purified by using such as the chromatography and tetra-O-acetyl intermediate (6) can be obtained, and then this intermediate is deprotected in a potassium hydroxide aqueous solution to obtain the intended compound (2).

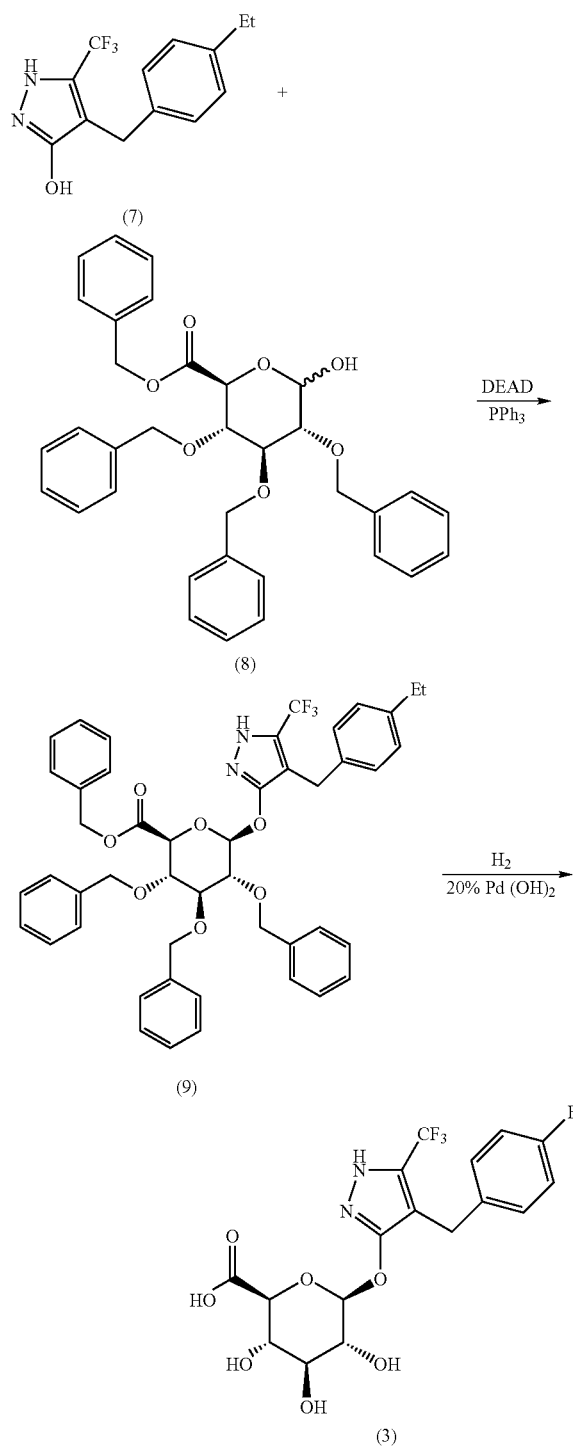

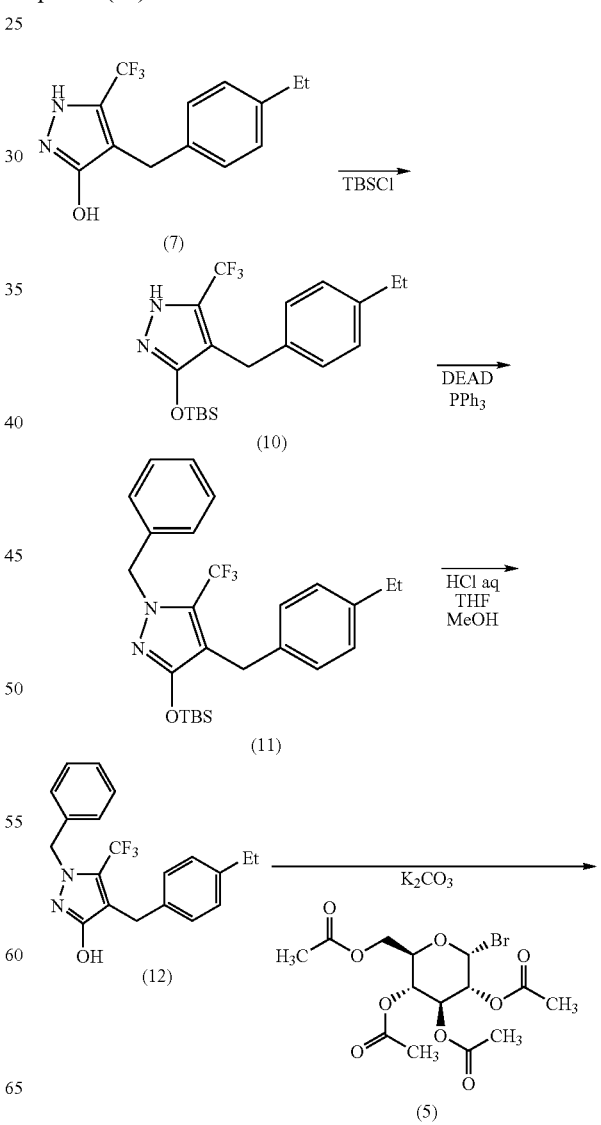

chromatography and tetra-benzyl intermediate (9) can be obtained. Then this intermediate is deprotected under hydrogen atmosphere by 20% Pd(OH)₂ to obtain the intended compound (3).

For example, the compound shown as the compound (15) of the present invention can be obtained by methods described as follows. A hydroxyl group of 1,2-dihydro-4-[(4-ethylphenyl)methyl]-5-(trifluoromethyl)-3H-pyrazole-3-one (7) is protected by tert-butyldimethylsilylchloride to obtain compound (10). Benzyl alcohol is reacted with a nitrogen atom on pyrazole of the compound in accordance with Mitsunobu reaction to obtain (11). TBS group is then deprotected by diluted hydrochloric acid and reacted with 2,3,4,6-tetra-O-acetyl-α-D-glucopyranosyl bromide (5) in the presence of potassium carbonate in chloroform-water overnight. The product is purified by using such as the chromatography and tetra-O-acetyl intermediate (13) can be obtained. Then this intermediate is deprotected in a potassium hydroxide aqueous solution to obtain (14). A primary hydroxyl group of the obtained compound (14) is reacted with methyl chlorocarbonate to obtain the intended compound (15).

For example, the compound shown as the compound (3) of the present invention can be obtained by methods described as follows. 1,2-dihydro-4-[(4-ethylphenyl)methyl]-5-(trifluoromethyl)-3H-pyrazole-3-one (7) (prepared by methods described in J. Med. Chem. 1996, 39, 3920-3928) and 2,3,4-tri-O-benzyl-D-glucopyranoside uronic acid benzyl ester (8) are reacted with triphenylphosphane and diethyl azodicarboxylate (DEAD) in tetrahydrofuran for 1.5 hours. The product is purified by using such as the

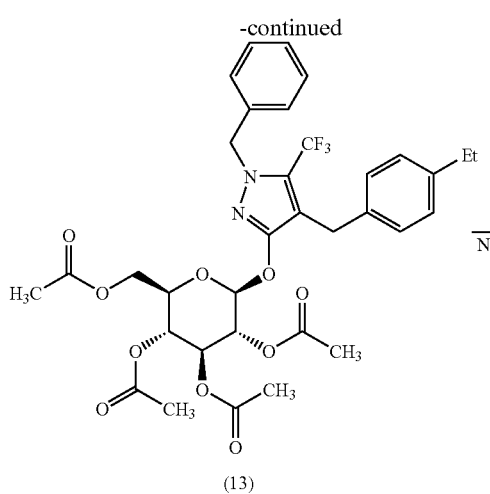

(13)

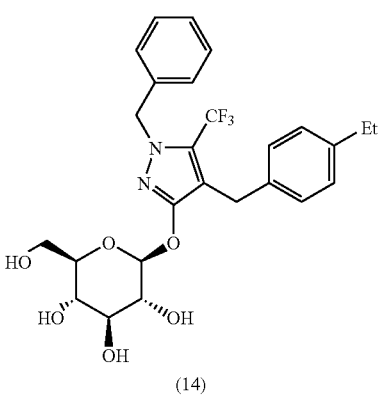

(14)

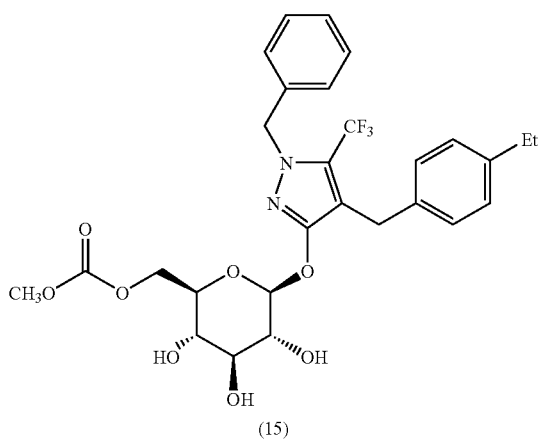

(15)

of pyrazole thereof is isopropylated by cesium carbonate and isopropyl iodide to obtain compound (19). A benzyl-protecting group of (19) is deprotected under hydrogen atmosphere by 20% Pd(OH)$_2$ to obtain compound (20), and a hydroxyl group at the 6th position of (20) is reacted with methyl chlorocarbonate in collidine to obtain the intended compound (21).

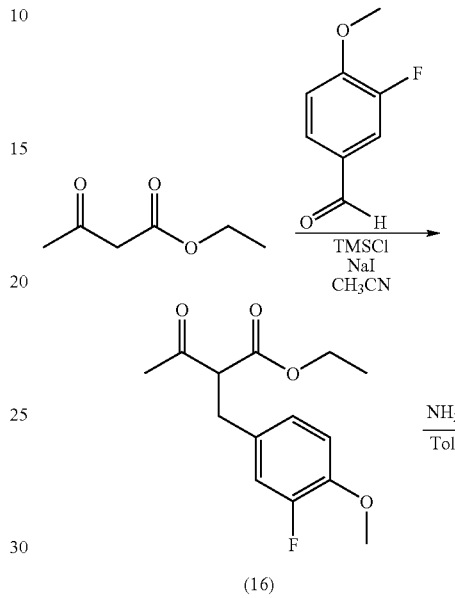

(16)

(17)

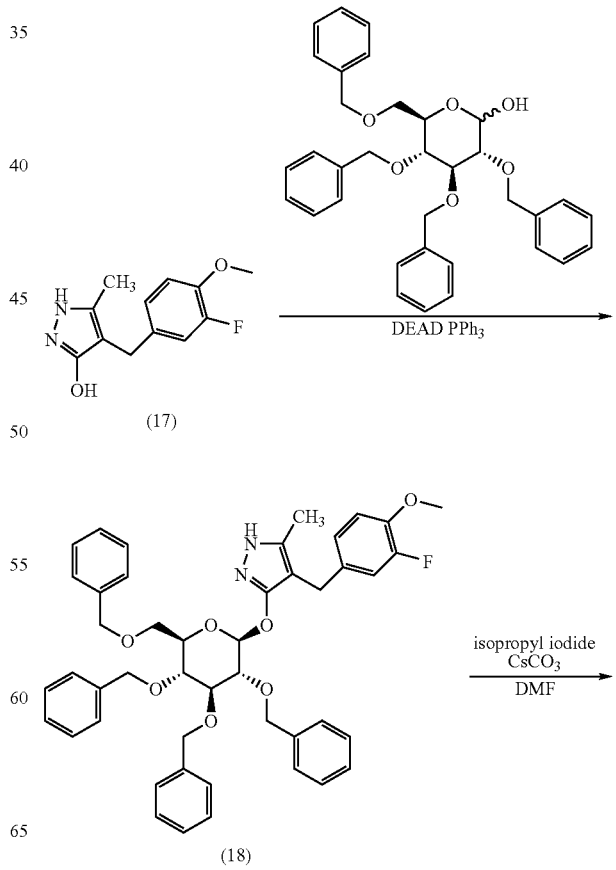

(18)

For example, the compound shown as the compound (21) of the present invention can be obtained by methods described as follows. Ethyl acetoacetate and 3-fluoro-4-methoxybenzaldehyde are reacted with trimethylsilylchloride and sodium iodide in acetonitrile to obtain an intermediate (16) and by forming a ring structure with hydrazine, 1,2-dihydro-4-[(3-fluoro-4-methoxyphenyl)methyl]-5-methyl-3H-pyrazole-3-one (17) can be obtained. Then, 2,3,4,6-tetrabenzylglucopyranose is reacted with a hydroxyl group on pyrazole thereof in accordance with Mitsunobu reaction to obtain (18) and a nitrogen atom in the 1st position -continued

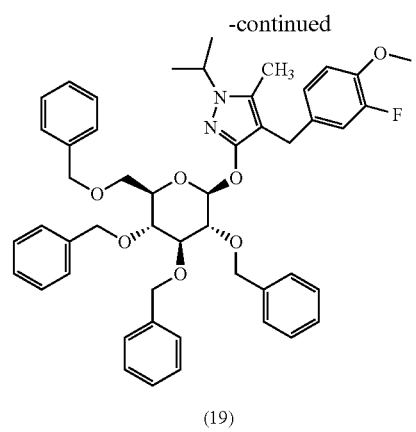
(19)

H₂
20%
Pd(OH)₂
→

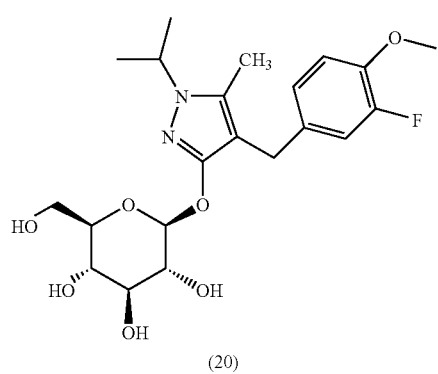
(20)

ClCOOCH₃
Collidine
→

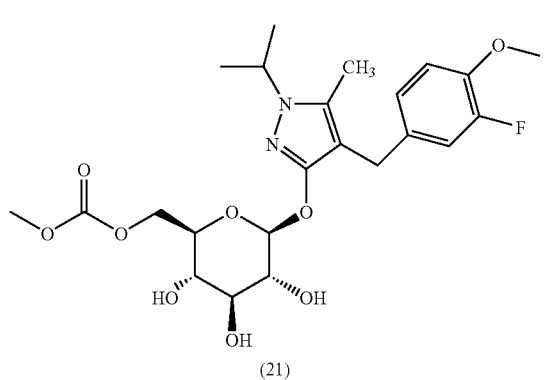
(21)

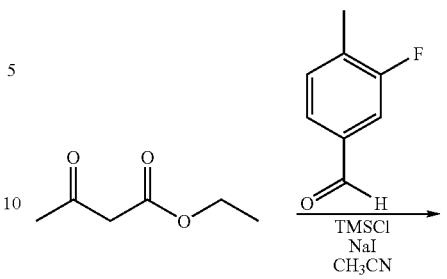

TMSCl
NaI
CH₃CN
→

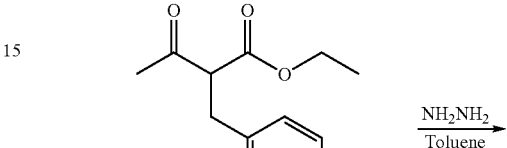
(22)

NH₂NH₂
Toluene
→

(23)

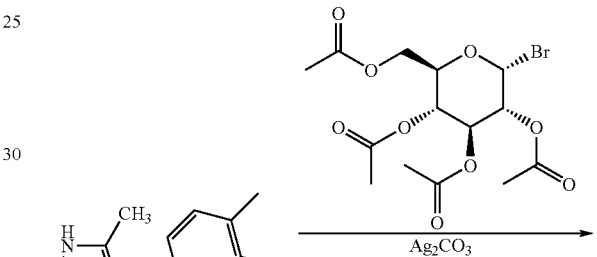

Ag₂CO₃
→

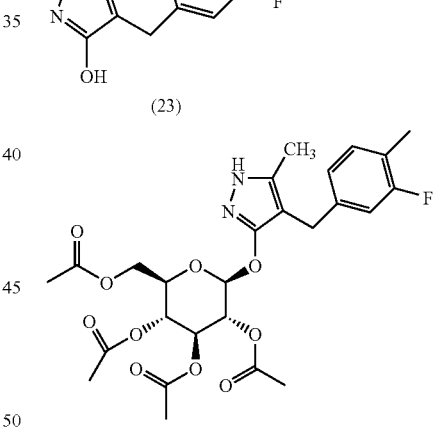
(24)

isopropyl iodide
CsCO₃
DMF
→

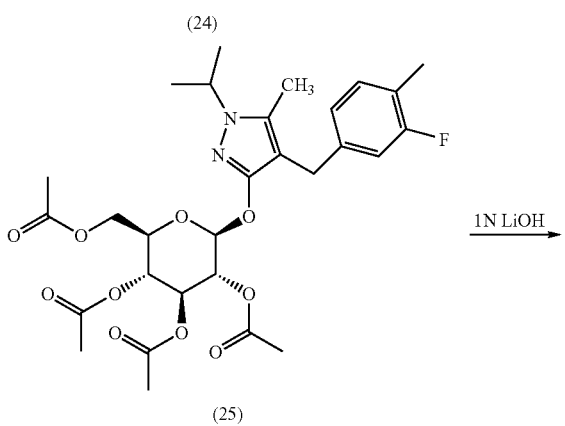
(25)

1N LiOH
→

For example, the compound shown as the compound (27) of the present invention can be obtained by methods described as follows. Ethyl acetoacetate and 3-fluoro-4-methylbenzaldehyde are reacted with trimethylsilylchloride and sodium iodide in acetonitrile to obtain an intermediate (22) and by forming a ring structure with hydrazine, 1,2-dihydro-4-[(3-fluoro-4-methylphenyl)methyl]-5-methyl-3H-pyrazole-3-one (23) can be obtained. Then, 2,3,4,6-O-tetraacetyl-α-D-glucopyranosyl bromide is reacted with hydroxyl group on pyrazole thereof by silver carbonate to obtain (24) and a nitrogen atom at the 1st position of pyrazole thereof is isopropylated by cesium carbonate and isopropyl iodide to obtain compound (25). An acetyl-protecting group of compound (25) is deprotected by 1N LiOH to obtain compound (26), and a hydroxyl group at the 6th position of compound (26) is reacted with methyl chlorocarbonate in collidine to obtain the intended compound (27).

-continued

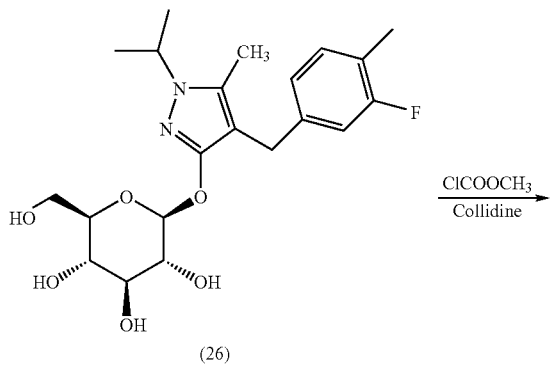

(26)

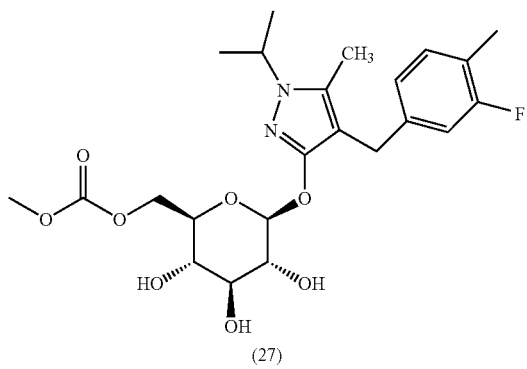

(27)

Pyrazole-O-glycoside derivatives and pyrazole-O-glucuronide derivatives of the present invention produced by the above-mentioned methods can be easily isolated and purified from the reaction mixture by ordinary methods for isolation and purification, such as the extraction by solvents, chromatography and crystallization.

A hydroxyl group of the compounds of the present invention may be substituted with appropriate substituents which are exchanged to a hydroxy group in vivo. The substituents of hydroxyl group are, for example, acyl group and carbamate group. An acyl group includes such as alkanoyl group having 2 to 20 carbon atoms and benzoyl group and carbamate group includes such as lower alkoxycarbonyl group. Especially, the substituents of hydroxyl group of glucopyranosyl group are preferably carbamate group which is lower alkoxycarbonyl group and more preferably methoxycarbonyl group. A carboxyl group of the compounds of the present invention may be substituted with appropriate substituents which are exchanged to a carboxyl group in vivo. The substituents of carboxyl group are, for example, lower alkyl group such as methyl group and ethyl group.

When the compounds shown in general formula (1A) or (1B) of the present invention can form salts thereof, the salts should be pharmaceutically acceptable. When an acidic group exists in the formula, the salts to the acidic group include such as ammonium salt; salts of alkali metal like sodium and potassium; salts of alkali earth metal like calcium and magnesium; aluminum salt; zinc salt; salts of organic amine like triethylamine, ethanolamine, morpholine, piperidine and dicyclohexylamine and salts of basic amino acid like arginine and lysine. When a basic group exists in the formula, the salts to the basic group include such as salts of inorganic acid like hydrochloric acid, sulfuric acid and phosphoric acid; salts of organic carboxylic acid like oxalic acid, acetic acid, citric acid, malic acid, benzoic acid, malic acid, fumaric acid, tartaric acid, succinate and glutamic acid and salts of organic sulfonic acid like methanesulfonic acid and p-toluenesulfonic acid. The salts can be formed by combining the compounds of general formula (1A) or (1B) and necessary acid or base in the appropriate amount and ratio in a solvent and decomposer. They can be also obtained by the cation or anion exchange from the form of other salts.

The compounds of general formula (1A) or (1B) of the present invention include solvates such as hydrates and alcohol adducts.

In the present invention, an inhibitor having the compounds of general formula (1A) or (1B) or salts thereof as an active ingredient can be used as pharmaceutical compositions, in particular, for the treatment of diabetes.

In the present invention, when the pyrazole-O-glycoside derivatives and pyrazole-O-glucuronide derivatives are used as the pharmaceutical compositions, for example, diabetic medicine, they can be given by oral or parenteral administration such as intramuscular, hypodermic and intravenous administrations and suppository. Though the dosage given for the above-mentioned purpose is determined depending on the therapeutic effect, administration method, treatment period, age and weight of the patient, the daily dose for adults is usually 1 μg to 10 g by oral administration and 0.01 μg to 1 g by parenteral administration.

Further, when pyrazole-O-glycoside derivatives and pyrazole-O-glucuronide derivatives of the present invention are prepared as an oral preparation, they can be prepared by ordinary methods after adding diluent bases and, if necessary, binders, disintegrants, lubricants, coloring agents and flavoring agents, in the form of tablets, powders, pills, granules, capsules, suppositories, solutions, dragees, depots or syrups. Diluent bases include such as lactose, cornstarch, sucrose, glucose, sorbit and crystalline cellulose; Binders include such as polyvinyl alcohol, polyvinyl ether, ethyl cellulose, methyl cellulose, gum arabic, tragacanth, gelatin, shellac, hydroxypropyl cellulose, hydroxypropyl starch and polyvinylpyrrolidone; Disintegrants include such as starch, gelatin powder, crystalline cellulose, calcium carbonate, sodium hydrogen carbonate, calcium citrate, dextran and pectin; Lubricants include such as magnesium stearate, talc, polyethylene glycols, silica and hardened vegetable oil; Coloring agents include those whose addition to pharmaceutical compounds is permitted; Flavoring agents includes such as cocoa powder, menthol, aromatic acid, mentha oil, borneol and cassia powder. Their tablets and granules may be coated with sugar, gelatin and other coating agents, if necessary.

When injectable solutions are prepared, they can be prepared by ordinary methods after adding pH adjuster, buffering agents, stabilizing agents and preserving agents, if necessary, in the form of hypodermic, intramuscular, and intravenous injectable solutions.

EXAMPLES

The following Examples will further illustrate the present invention. They are preferred embodiments of the present invention, which by no means limit the invention.

Example 1

Synthesis of 4-((4-methylthiophenyl)methyl)-5-(trifluoromethyl)-1H-pyrazole-3-O-β-D-glucopyranoside Process 1

Synthesis of 4'-((4'-methylthiophenyl)methyl)-5'-(trifluoromethyl)-1H-pyrazole-3'-O-(2,3,4,6-O-tetraacetyl)-β-D-glucopyranoside 519 mg (1.80 mmol) of 1,2-dihydro-4-((4-methylthiophenyl)methyl)-5-(trifluoromethyl)-3H-pyrazole-3-one (prepared by methods described in J. Med. Chem. 1996, 39, 3920-3928), 1.258 g (3.06 mmol) of 2,3,4,6-O-tetraacetyl-α-D-glucopyranosyl bromide, 112 mg (0.36 mmol) of benzyl tri-n-butylammonium chloride and 1.244 g (9.0 mmol) of potassium carbonate were stirred at room temperature for 21 hours after adding 0.1 mL of water and 4 mL of chloroform. After the reaction was completed, the mixture was controlled by 10% hydrochloric acid to show pH 7. After adding 5 mL of chloroform and removing water layer, organic layer was washed with 4 mL of saturated sodium bicarbonate aqueous solution and 4 mL of saturated aqueous sodium chloride solution, respectively. After the product was dried with magnesium sulfate and concentrated, it was purified by silica gel column chromatography (chloroform:methanol=20:1 (V/V)) to obtain 870 mg (1.41 mmol) of 4'-((4'-methylthiophenyl)methyl)-5'-(trifluoromethyl)-1H-pyrazole-3'-O-(2,3,4,6-O-tetraacetyl)-β-D-glucopyranoside in the form of pale yellow oily product.

$^1$H-NMR (300 MHz, DMSO-d6) δ: 1.92 (3H, s), 2.03 (3H, s), 2.05 (3H, s), 2.10 (3H, s), 2.45 (3H, s), 3.74 (2H, s), 4.21 (1H, dd, J=2.4, 12.6 Hz), 4.28 (1H, dd, J=4.2, 12.6 Hz), 5.19-5.28 (4H, m), 5.41 (1H, d, J=6.3 Hz), 7.09 (2H, d, J=8.1 Hz), 7.16 (2H, d, J=8.1 Hz). ESI-MS(m/z): 619[(M+H)$^+$], 617[(M−H)$^−$]

Process 2

Synthesis of 4-((4-methylthiophenyl)methyl)-5-(trifluoromethyl)-1H-pyrazole-3-O-β-D-glucopyranoside 804 mg (1.30 mmol) of 4'-((4'-methylthiophenyl)methyl)-5'-(trifluoromethyl)-1H-pyrazole-3'-O-(2,3,4,6-O-tetraacetyl)-β-D-glucopyranoside in the form of pale yellow oil was dissolved in 6 mL of ethanol. 0.8 mL of 50% aqueous solution of potassium hydroxide was added thereto and the mixture was stirred at room temperature for 10 minutes. After the reaction was completed, the mixture was controlled by 10% hydrochloric acid to show pH 7 and further stirred for 24 hours. Crystals thus formed were taken by filtration and washed with 5 mL of ethanol. Then the oily product obtained by concentrating the washings was purified by silica gel column chromatography (chloroform:methanol=10:1 (V/V)) to obtain 321 mg (0.71 mmol) of 4-((4-methylthiophenyl)methyl)-5-(trifluoromethyl)-1H-pyrazole-3-O-β-D-glucopyranoside in the form of white crystals.

$^1$H-NMR (300 MHz, DMSO-d6) δ: 2.43 (3H, s), 3.15-3.25 (4H, m), 4.39 (1H, dd, J=5.3, 12.0 Hz), 3.67 (1H, d, J=12.0), 3.75 (2H, s), 4.92 (1H, br-s), 5.04 (1H, br-s), 5.12 (1H, br-s), 7.12 (2H, d, J=8.7 Hz), 7.16 (2H, d, J=8.7 Hz). ESI-MS(m/z): 449[(M−H)$^−$]

Example 2

Synthesis of 4-((4-ethylphenyl)methyl)-5-(trifluoromethyl)-1H-pyrazole-3-yl-O-β-D-glucopyranoside uronic acid Process 1

Synthesis of benzyl 4'-[(4'-ethylphenyl)methyl]-5'-(trifluoromethyl)-1H-pyrazole-3'-yl-2,3,4-0-tribenzyl-β-D-glucopyranouronate 199 mg (0.359 mmol) of 2,3,4-tri-0-benzyl-D-glucopyranoside uronic acid benzyl ester (SIGMA), 99 mg (0.367 mmol) of 1,2-dihydro-4-((4-ethylphenyl)methyl)-5-(trifluoromethyl)-3H-pyrazole-3-one (prepared by methods described in J. Med. Chem. 1996, 39, 3920-3928) and 109 mg (0.416 mmol) of triphenylphosphane were dissolved in 0.5 ml of dried THF (not containing stabilizer). 0.18 ml (0.40 mmol) of 40% toluene solution of diethyl azodicarboxylate was added thereto under cooling with ice and the mixture was stirred at room temperature for 1.5 hours. The reaction mixture was directly purified by silica gel chromatography (hexane~ethyl acetate:hexane=1:10~1:5) and concentrated under reduced pressure to obtain 127 mg (0.157 mmol) of benzyl 4'-[(4'-ethylphenyl)methyl]-5'-(trifluoromethyl)-1H-pyrazole-3'-yl-2,3,4-0-tribenzyl-β-D-glucopyranouronate in the form of pale yellow oily product.

$^1$H-NMR (300 MHz, DMSO-d6) δ: 1.12 (3H, t, J=7.8 Hz), 2.50 (2H, q, J=7.8 Hz), 3.64-3.86 (4H, m), 3.90-4.02 (1H, m), 4.05-4.20 (1H, m), 4.40-4.58 (3H, m), 4.65-4.82 (3H, m), 5.10 (1H, d, J=12.1 Hz), 5.15 (1H, d, J=12.1 Hz), 5.20-5.30 (1H, br), 6.90-7.35 (24H, m)

Process 2

Synthesis of 4-((4-ethylphenyl)methyl)-5-(trifluoromethyl)-1H-pyrazole-3-yl-O-β-D-glucopyranoside uronic acid 122 mg (0.151 mmol) of benzyl 4'-[(4'-ethylphenyl)methyl]-5'-(trifluoromethyl)-1H-pyrazole-3'-yl-2,3,4-0-tribenzyl-β-D-glucopyranouronate was dissolved in 4 ml of ethyl acetate and 4 ml of methanol and, in the presence of 204 mg of 20%-palladium hydroxide-carbon (50% wet, Aldrich) under hydrogen atmosphere at normal pressures, stirred at room temperature for 8 hours. After filtrating 20%-palladium hydroxide-carbon and washing the mixture with 100 ml of dichloromethane:methanol (4:1), the filtrate was evaporated under reduced pressure. The obtained solid substance was suspended in the distilled water and purified by SedPack column (water:methanol=1:0~0:1). Then the product was evaporated under reduce pressure at 40° C. in the bath or lower to obtain 22 mg (0.050 mmol) of 4-[(4-ethylphenyl)methyl]-5-(trifluoromethyl)-1H-pyrazole-3-yl-β-D-glucopyranoside uronic acid in the form of amorphous white solid substance.

$^1$H-NMR (300 MHz, DMSO-d6) δ: 1.19 (3H, t, J=7.5 Hz), 2.58 (2H, q, J=7.5 Hz), 3.35-3.51 (2H, m), 3.52-3.65 (1H, m), 3.70-3.90 (3H, m), 5.00-5.20 (1H, br), 7.06 (2H, d, J=8.41 Hz), 7.09 (2H, d, J=8.4 Hz) ESI-MS(m/z) 445[(M−H)$^+$], 447[(M+H)$^+$]

Example 3

Synthesis of 4'-[(4'-ethylphenyl)methyl]-1'-benzyl-5'-trifluoromethyl-1H-pyrazole-3'-O-β-D-glucopyranoside Process 1

Synthesis of 4-[(4-ethylphenyl)methyl]-5-trifluoromethyl-3-O-t-butyldimethylsilyl-1H-pyrazole 4.76 g (17.6 mmol) of 1,2-dihydro-4-[(4-ethylphenyl)methyl]-5-trifluoromethyl-3H-pyrazole-3-one (prepared by methods described in J. Med. Chem. 1996, 39, 3920-3928) and 1.57 g (23.1 mmol) of imidazole were dissolved in 20 ml of dimethylformamide. 2.98 g (19.8 mmol) of t-butyldimethylsilylchloride was added thereto and the mixture was stirred at room temperature for 30 minutes. After adding 100 ml of water, the mixture was extracted with a mixed solution of ethyl acetate-hexane (2:1) three times. The organic layer was washed with water, dried over sodium sulfate and concentrated to obtain 6.9 g of the intended product (17.9 mmol, quantitative).

$^1$H-NMR (300 MHz, CDCl$_3$) δ: 0.21 (6H, s), 0.93 (9H, s), 1.19 (3H, t, J=7.6 Hz), 2.59 (2H, q, J=7.6 Hz), 3.74 (2H, s), 7.09 (4H, pseudo ABq) ESI-MS(m/z) 269 [(M−TBS)$^-$]

Process 2

Synthesis of 4-[(4-ethylphenyl)methyl]-1-benzyl-5-trifluoromethyl-3-O-t-butyldimethylsilyl-1H-pyrazole 0.39 g (1.0 mmol) of 4-[(4-ethylphenyl)methyl]-5-trifluoromethyl-3-O-t-butyldimethylsilyl-1H-pyrazole, 0.30 g (1.1 mmol) of triphenylphosphane and 0.14 ml (1.4 mmol) of benzyl alcohol were dissolved in 2.0 ml of anhydrous tetrahydrofuran and stirred at room temperature. 0.50 ml (1.1 mmol) of 40% toluene solution of diethyl azodicarboxylate was slowly added thereto and, 20 minutes later, the mixture was concentrated. Then 1 ml of hexane was added, and formed sediments were taken by filtration, concentrated and purified by silica gel column (hexane→5% ethyl acetate/hexane) to obtain 0.40 g (0.83 mmol) of the intended product (83%).

$^1$H-NMR (300 MHz, CDCl$_3$) δ: 0.22 (6H, s), 0.92 (9H, s), 1.20 (3H, t, J=7.5 Hz), 2.59 (2H, q, J=7.5 Hz), 3.74 (2H, s), 5.19 (2H, s), 7.06 (4H, pseudo ABq), 7.11-7.33 (5H, m)

Process 3

Synthesis of 4-[(4-ethylphenyl)methyl]-1-benzyl-5-trifluoromethyl-1H-pyrazole 0.40 g (0.83 mmol) of 4-[(4-ethylphenyl)methyl]-1-benzyl-5-trifluoromethyl-3-O-t-butyldimethylsilyl-1H-pyrazole was dissolved in 2 ml of tetrahydrofuran and 0.5 ml of methanol and 1 ml of 1M-HCl aqueous solution was added thereto and the mixture was stirred at room temperature for 7 hours. After adding 5 ml of water, the mixture was extracted with 5 ml of ethyl acetate three times. The product was dried over sodium sulfuric anhydride, concentrated and purified by silica gel column (hexane→10% ethyl acetate/hexane) to obtain 0.27 g (0.74 mmol) of the intended product (89%).

$^1$H-NMR (300 MHz, CDCl$_3$) δ: 1.21 (3H, t, J=7.6 Hz), 2.61 (2H, q, J=7.6 Hz), 3.77 (2H, s), 5.18 (2H, s), 7.07-7.31 (9H, m) ESI-MS(m/z) [361 (M+H)$^+$], [359 (M−H)$^-$]

Process 4

Synthesis of 4'-[(4-ethylphenyl)methyl]-1'-benzyl-5'-trifluoromethyl-1H-pyrazole-3'-O-(2,3,4,6-tetraacetyl)-β-D-glucopyranoside 1 mL of water and 10 mL of chloroform were added to 0.22 g (0.62 mmol) of 4-[(4-ethylphenyl)methyl]-1-benzyl-5-trifluoromethyl-1H-pyrazole, 0.39 g (0.94 mmol) of 2,3,4,6-O-tetraacetyl-α-D-glucopyranosyl bromide, 0.055 g (0.18 mmol) of benzyl tri-n-butylammonium chloride, 0.79 g (5.7 mmol) of potassium carbonate and the mixture was stirred at room temperature overnight. About 0.1 g of benzyl tri-n-butylammonium chloride was added thereto and the mixture was further stirred overnight. The organic layer was purified by silica gel column chromatography (ethyl acetate:hexane=10:1) to obtain 0.39 of roughly purified substance containing the intended product mainly and the further reaction proceeded.

$^1$H-NMR (300 MHz, CDCl$_3$) δ: 1.19 (3H, t, J=7.6 Hz), 1.86 (3H, s), 2.015 (3H, s), 2.019 (3H, s), 2.03 (3H, s), 2.58 (2H, q, J=7.6 Hz), 3.74 (2H, s), 3.81 (1H, ddd, J=9.5, 4.2, 2.3 Hz), 4.08 (1H, dd, J=12.5, 2.3 Hz), 4.27 (1H, dd, J=12.5, 4.2 Hz), 5.16-5.28 (3H, m), 5.24 (2H, s), 5.58-5.63 (1H, m), 7.05 (4H, s), 7.16-7.35 (5H, m) ESI-MS(m/z) [691 (M+H)$^+$]

Process 5

Synthesis of 4-[(4-ethylphenyl)methyl]-1-benzyl-5-trifluoromethyl-1H-pyrazole-3-O-β-D-glucopyranoside 0.28 g of roughly purified substance of 4'-[(4'-ethylphenyl)methyl]-1'-benzyl-5'-trifluoromethyl-1H-pyrazole-3'-O-(2,3,4,6-tetraacetyl)-β-D-glucopyranoside was dissolved in 5 ml of ethanol and 5 ml of 4N NaOH aqueous solution was added thereto and the mixture was stirred at room temperature. 1 hour later, 50 ml of water was added and the mixture was extracted with ethyl acetate five times. Then the product was concentrated and purified by silica gel column (dichloromethane→10% methanol/dichloromethane) to obtain 0.11 g (0.21 mmol) of the intended product.

$^1$H-NMR (300 MHz, CD3OD) δ: 1.19 (3H, t, J=7.6 Hz), 2.58 (2H, q, J=7.6 Hz), 3.34-3.46 (4H, m), 3.68 (1H, dd, J=12.0, 4.7 Hz), 3.81 (1H, dd, J=12.0, 2.1 Hz), 3.83 (2H, s), 5.32 (2H, s), 5.34-5.37 (1H, m), 7.07 (4H, s), 7.10-7.12 (2H, m), 7.25-7.33 (3H, m)

Example 4

Synthesis of 4'-[(4'-ethylphenyl)methyl]-1'-benzyl-5'-trifluoromethyl-1H-pyrazole-3'-O-(6-carbomethoxy)-β-D-glucopyranoside 0.11 g (0.21 mmol) of 4'-[(4'-ethylphenyl)methyl]-1'-benzyl-5'-trifluoromethyl-1H-pyrazole-3'-O-β-D-glucopyranoside was dissolved in 1.5 ml of pyridine and cooled in the ice bath. 0.020 ml (0.26 mmol) of methyl chlorocarbonate was added thereto and the temperature of the mixture was raised up to room temperature in 0.5 hour. 0.020 ml (0.26 mmol) of methyl chlorocarbonate was further added 2 hours later and 19 hours later, then the mixture was stirred at room temperature for 6 hours. 5 ml of ethyl acetate, 10 ml of 1M HCl aqueous solution and 20 ml of water were added thereto and the mixture was extracted with ethyl acetate. Then the product was dried, concentrated and purified by silica gel column (ethyl acetate) to obtain 0.059 g (0.10 mmol) of the intended product (47%).

¹H-NMR (300 MHz, CDCl3) δ: 1.18 (3H, t, J=7.6 Hz), 2.57 (2H, q, J=7.6 Hz), 3.48-3.60 (4H, m), 3.70 (3H, s), 3.74 (1H, d, J=15.8 Hz), 3.82 (1H, d, J=15.8 Hz), 4.34 (2H, s), 5.22 (1H, d, J=4.4 Hz), 5.23 (2H, s), 7.07 (4H, s), 7.12 (2H, d, J=6.4 Hz), 7.21-7.32 (3H, m) ESI-MS(m/z) [581 (M+H)⁺], [579 (M−H)⁻]

Example 5

Synthesis of 4-[(4-ethylphenyl)methyl]-1-[(4-methoxyphenyl)methyl]-5-trifluoromethyl-1H-pyrazole-3-O-β-D-glucopyranoside Process 1

Synthesis of 4-[(4-ethylphenyl)methyl]-1-[(4-methoxyphenyl)methyl]-5-trifluoromethyl-3-O-t-butyldimethylsilyl-1H-pyrazole The intended product was obtained in the same manner as shown in Process 2 of Example 3, by using 4-methoxy benzyl bromide instead of benzyl bromide.

¹H-NMR (300 MHz, CDCl₃) δ: 0.22 (6H, s), 0.93 (9H, s), 1.19 (3H, t, J=7.6 Hz), 2.58 (2H, q, J=0.6 Hz), 3.72 (2H, s), 3.78 (3H, s), 5.14 (2H, s), 6.83 (2H, d, J=8.8 Hz), 7.07 (4H, pseudo ABq), 7.16 (2H, d, J=8.8 Hz)

Process 2

Synthesis of 4-[(4-ethylphenyl)methyl]-1-[(4-methoxyphenyl)methyl]-5-(trifluoromethyl)-1H-pyrazole The intended product was obtained (82%) from 4-[(4-ethylphenyl)methyl]-1-[(4-methoxyphenyl)methyl]-5-(trifluoromethyl)-3-O-t-butyldimethylsilyl-1H-pyrazole in the same manner as shown in Process 3 of Example 3

¹H-NMR (300 MHz, CDCl₃) δ: 1.21 (3H, t, J=7.5 Hz), 2.60 (2H, q, J=7.5 Hz), 3.77 (5H, s), 5.10 (2H, s), 6.81-6.84 (2H, m), 7.07-7.19 (6H, m) ESI-MS(m/z) [391 (M+H)⁺], [389 (M−H)⁻]

Process 3

Synthesis of 4'-[(4'-ethylphenyl)methyl]-1'-[(4-methoxyphenyl)methyl]-5'-trifluoromethyl-1H-pyrazole-3'-O-(2,3,4,6-tetraacetyl)-β-D-glucopyranoside The roughly purified product of the intended product was obtained from 4-[(4-ethylphenyl)methyl]-1-[(4-methoxyphenyl)methyl]-5-(trifluoromethyl)-1H-pyrazole in the same manner as shown in Process 4 of Example 3.

¹H-NMR (300 MHz, CDCl₃) δ: 1.19 (3H, t, J=7.6 Hz), 1.86 (3H, s), 2.07 (3H, s), 2.11 (6H, s), 2.58 (2H, q, J=7.6 Hz), 3.73 (2H, s), 3.75-3.84 (1H, m), 4.24-4.30 (1H, m), 5.16 (2H, s), 5.19-5.28 (3H, m), 5.56-5.60 (1H, m), 6.75 (2H, d, J=8.8 Hz), 7.05 (4H, s), 7.15 (2H, d, J=8.8 Hz) ESI-MS(m/z) [721(M+H)⁺]

Process 4

Synthesis of 4-[(4-ethylphenyl)methyl]-1-[(4-methoxyphenyl)methyl]-5-trifluoromethyl-1H-pyrazole-3-O-β-D-glucopyranoside The intended product was obtained (91% in 2 steps) from 4'-[(4'-ethylphenyl)methyl]-1'-[(4-methoxyphenyl)methyl]-5'-trifluoromethyl-1H-pyrazole-3'-O-(2,3,4,6-tetraacetyl)-β-D-glucopyranoside in the same manner as shown in Process 5 of Example 3.

¹H-NMR (300 MHz, CD3OD) δ: 1.19 (3H, t, J=7.6 Hz), 2.57 (2H, q, J=7.6 Hz), 3.36-3.44 (4H, m), 3.66-3.82 (2H, m), 3.76 (3H, s), 3.82 (2H, s), 5.24 (2H, s), 5.33-5.36 (1H, m), 6.86 (2H, d, J=8.5 Hz), 7.07 (4H, s), 7.12 (2H, d, J=8.5 Hz) ESI-MS(m/z) [553 (M+H)⁺], [551 (M−H)⁻]

Example 6

Synthesis of 4'-[(4'-ethylphenyl)methyl]-1'-[(4'-methoxyphenyl)methyl]-5'-trifluoromethyl-1H-pyrazole-3'-O-(6-carbomethoxy)-β-D-glucopyranoside 0.18 g (0.32 mmol) of 4-[(4-ethylphenyl)methyl]-1-[(4-methoxyphenyl)methyl]-5-trifluoromethyl-1H-pyrazole-3-O-β-D-glucopyranoside was dissolved in 2 ml of 2,4,6-collidine and cooled down to −50° C. 0.035 ml (0.45 mmol) of methyl chlorocarbonate was added thereto and the temperature of the mixture was raised up to room temperature in 1 hour. 27 hours later, 20 ml of ethyl acetate and 20 ml of 1M HCl aqueous solution were added thereto and the mixture was extracted with ethyl acetate. Then the product was dried, concentrated and purified by silica gel column (hexane→ethyl acetate) to obtain 0.12 g (0.20 mmol) of the intended product (62%).

¹H-NMR (300 MHz, CDCl₃) δ: 1.21 (3H, t, J=7.6 Hz), 2.26 (1H, d, J=2.3 Hz), 2.61 (2H, q, J=7.6 Hz), 2.69 (1H, s), 2.86 (1H, s), 3.45-3.61 (4H, m), 3.73 (1H, d, J=15.2 Hz), 3.80 (3H, s), 3.80 (3H, s), 3.88 (1H, d, J=15.2 Hz), 4.37 (1H, d, J=12.3 Hz), 4.49 (1H, dd, J=12.3, 3.0 Hz), 5.19 (2H, s), 5.20 (1H, d, J=7.6 Hz), 6.86 (2H, d, J=8.5 Hz), 7.10 (4H, s), 7.16 (2H, d, J=8.5 Hz)

Example 7

Synthesis of 4-[(4-ethylphenyl)methyl]-1-phenyl-5-trifluoromethyl-1H-pyrazole-3-O-β-D-glucopyranoside Process 1

Synthesis of 4-[(4-ethylphenyl)methyl]-1-phenyl-5-trifluoromethyl-3-O-t-butyldimethylsilyl-1H-pyrazole 0.079 g (0.21 mmol) of 4-[(4-ethylphenyl)methyl]-5-trifluoromethyl-3-O-t-butyldimethylsilyl-1H-pyrazole, 0.049 g (0.40 mmol) of phenylboronic acid and 0.057 g (0.32 mmol) of copper acetate anhydride were dissolved in 5 ml of dried dichloromethane. 0.15 g of molecular sieves 4A powder and 0.032 ml (0.40 mmol) of pyridine were added thereto and the mixture was stirred at room temperature overnight. Then the reaction mixture was purified by silica gel column (hexane→hexane:dichloromethane=5:1~3:1) and the main product was separated to obtain 0.074 g (0.16 mmol) of the intended product (80%).

¹H-NMR (300 MHz, CDCl₃) δ: 0.27 (6H, s), 0.96 (9H, s), 1.21 (3H, t, J=7.6 Hz), 2.61 (2H, q, J=7.6 Hz), 3.84 (2H, s), 7.11 (2H, J=8.3 Hz), 7.18 (2H, J=8.3 Hz), 7.35-7.45 (5H, m) ESI-MS(m/z) [461 (M+H)⁺], [459 (M−H)⁻]

Process 2

Synthesis of 4-[(4-ethylphenyl)methyl]-1-phenyl-5-trifluoromethyl-1H-pyrazole

The intended product was obtained (95%) from 4-[(4-ethylphenyl)methyl]-1-phenyl-5-(trifluoromethyl)-3-O-t-butyldimethylsilyl-1H-pyrazole in the same manner as shown in Process 3 of Example 3.

$^1$H-NMR (300 MHz, CDCl$_3$) δ: 1.22 (3H, t, J=7.6 Hz), 2.62 (2H, q, J=7.6 Hz), 3.81 (2H, s), 7.10 (2H, d, J=8.1 Hz), 7.17 (2H, d, J=8.1 Hz), 7.35-7.50 (5H, m), 10.40-10.80 (1H, br-s) ESI-MS(m/z) [347 (M+H)$^+$], [345 (M−H)−]

Process 3

Synthesis of 4'-[(4'-ethylphenyl)methyl]-1'-phenyl-5'-trifluoromethyl-1H-pyrazole-3'-O-(2,3,4,6-tetraacetyl)-β-D-glucopyranoside The roughly purified product of the intended product was obtained from 4-[(4-ethylphenyl)methyl]-1-phenyl-5-trifluoromethyl-1H-pyrazole in the same manner as shown in Process 4 of Example 3.

$^1$H-NMR (300 MHz, CDCl$_3$) δ: 1.21 (3H, t, J=7.6 Hz), 1.90 (3H, s), 2.02 (3H, s), 2.03 (3H, s), 2.04 (3H, s), 2.61 (2H, q, J=7.6 Hz), 3.80-3.90 (2H, s and 1H, m), 4.10-4.30 (2H, m), 5.15-5.36 (3H, m), 5.68 (1H, d, J=7.5 Hz), 7.10 (2H, d, J=8.3 Hz), 7.15 (2H, d, J=8.3 Hz), 7.38-7.47 (5H, m) ESI-MS(m/z) [677 (M+H)$^+$]

Process 4

Synthesis of 4-[(4-ethylphenyl)methyl]-1-phenyl-5-trifluoromethyl-1H-pyrazole-3-O-β-D-glucopyranoside The intended product was obtained (84% in 2 steps) from the roughly purified product of 4'-[(4'-ethylphenyl)methyl]-1'-phenyl-5'-trifluoromethyl-1H-pyrazole-3'-O-(2,3,4,6-tetraacetyl)-β-D-glucopyranoside in the same manner as shown in Process 5 of Example 3.

$^1$H-NMR (300 MHz, DMSO-d$_6$) δ: 1.19 (3H, t, J=7.6 Hz), 2.60 (2H, q, J=7.6 Hz), 3.15-3.35 (4H, m), 3.45-3.55 (1H, m), 3.69 (1H, dd, J=11.4, 5.7 Hz), 3.85 (1H, d, J=15.6 Hz), 3.92 (1H, d, J=15.6 Hz), 4.55 (1H, t, J=5.7 Hz), 5.03 (1H, d, J=4.5 Hz), 5.13 (1H, d, J=3.9 Hz), 5.35 (1H, d, J=7.5 Hz), 5.41 (1H, d, J=4.5 Hz), 7.17 (2H, d, J=8.3 Hz), 7.22 (2H, d, J=8.3 Hz), 7.47-7.62 (5H, m) ESI-MS(m/z) [509 (M+H)$^+$], [507 (M−H)$^-$]

Example 8

Synthesis of 4'-[(4'-ethylphenyl)methyl]-1'-phenyl-5'-trifluoromethyl-1H-pyrazole-3'-O-(6-carbomethoxy)-β-D-glucopyranoside The intended product was obtained (71%) from 4-[(4-ethylphenyl)methyl]-1-phenyl-5-trifluoromethyl-1H-pyrazole-3-O-β-D-glucopyranoside in the same manner as shown in Example 4.

$^1$H-NMR (300 MHz, CDCl$_3$) δ: 1.22 (3H, t, J=7.6 Hz), 2.18 (1H, br), 2.62 (2H, q, J=7.6 Hz), 2.72 (1H, br), 2.89 (1H, br), 3.45-3.63 (4H, m), 3.78 (3H, s), 3.81 (1H, d, J=15.6 Hz), 3.98 (1H, d, J=15.6 Hz), 4.37 (1H, dd, 12.0, 1.7 Hz), 4.49 (1H, dd, 12.0, 3.6 Hz), 5.32 (1H, d, J=7.2 Hz), 7.14 (2H, d, J=8.3 Hz), 7.19 (2H, d, J=8.3 Hz), 7.39-7.47 (5H, m) ESI-MS(m/z) [567 (M+H)+], [565 (M−H)−]

Example 9

Synthesis of 4-[(3-fluoro-4-methoxyphenyl)methyl]-1-isopropyl-5-methyl-1H-pyrazole-3-O-β-D-glucopyranoside Process 1

Synthesis of ethyl 2-[(3-fluoro-4-methoxy)benzyl]-3-oxobutyrate 1.69 g (13.0 mmol) of ethyl acetoacetate and 9.6 g (65 mmol) of sodium iodide were dissolved in 100 ml of acetonitrile and cooled down to 0° C. 8.2 ml (65 mmol) of trimethylsilylchloride was slowly added thereto and 10 minutes later, 2.0 g (13.0 mmol) of 3-fluoro-4-methoxybenzaldehyde was added in three times. 10 minutes later, the temperature of the mixture was raised up to room temperature and the mixture was continuously stirred. 6 hours later, the mixture was moved into the 60° C. bath and stirred overnight. After the reaction mixture was cooled down, 250 ml of water, 250 ml of ethyl acetate and 50 ml of saturated aqueous sodium chloride solution were added thereto, and ethyl acetate layer was extracted. The obtained organic layer was washed with saturated sodium sulfite aqueous solution and dried over anhydrous magnesium sulfate. Then the product was concentrated and purified by silica gel column chromatography (EtOAc-Hex; 1:4) to obtain 2.54 g (9.5 mmol) of the intended product (yield 73%).

$^1$H-NMR (300 MHz, CDCl$_3$) δ: 6.82-6.96 (3H, m), 4.12-4.20 (2H, m), 3.86 (3H, s), 3.71 (1H, t, J=7.8), 3.08 (2H, d, J=8.1), 2.20 (3H, s), 1.23 (3H, t, J=7.2).

Process 2

Synthesis of 1,2-dihydro-4-[(3-fluoro-methoxyphenyl)methyl]-5-methyl-3H-pyrazole-3-one 2.54 g (9.5 mmol) of ethyl 2-[(3-fluoro-4-methoxy)benzyl]-3-oxobutyrate was dissolved in 50 ml of toluene. 0.72 g (14.2 mmol) of hydrated hydrazine was added thereto and the mixture was stirred at 100° C. overnight. After the reaction mixture was cooled down, the formed white solid was filtrated and dried by a vacuum pump to obtain 1.86 g (7.9 mmol) of the intended product (yield 83%).

$^1$H-NMR (300 MHz, DMSO-d6) δ: 7.00 (1H, t, J=8.4), 6.86-6.94 (2H, m), 3.75 (3H, s), 3.46 (2H, s), 1.98 (3H, s). ESI-MS(m/z): 237[(M+H)$^+$], 235[(M−H)$^-$].

Process 3

Synthesis of 4'-[(3'-fluoro-4'-methoxyphenyl)methyl]-5'-methyl-1H-pyrazole-3'-O-(2,3,4,6-tetrabenzyl)-β-D-glucopyranoside 2.3 g (4.2 mmol) of 2,3,4,6-tetra-0-benzyl-D-glucopyranoside, 1.0 g (4.2 mmol) of 1,2-dihydro-4-[(3-fluoro-4-methoxyphenyl)methyl]-5-methyl-3H-pyrazole-3-one and 1.1 g (4.2 mmol) of triphenylphosphane were dissolved in 40 ml of dried THF (not containing stabilizer). 1.9 ml (4.2 mmol) of 40% toluene solution of diethyl azodicarboxylate was added thereto under cooling with ice and the mixture was stirred at room temperature overnight. After the reaction mixture was concentrated, the product was directly purified by silica gel column chromatography (hexane~ethyl acetate: hexane=2:3) and concentrated under reduced pressure to obtain 2.2 g (2.9 mmol) of the intended product (yield 70%).

¹H-NMR (300 MHz, CDCl₃) δ: 7.10-7.32 (20H, m), 6.78-6.92 (2H, m), 6.67 (1H, t, J=8.1), 5.51 (1H, d, J=7.5), 4.46-4.92 (10H, m), 3.60-3.76 (6H, m), 3.71 (3H, s), 2.07 (3H, s). ESI-MS(m/z): 759[(M+H)⁺], 757[(M−H)⁻].

Process 4

Synthesis of 4'-[(3'-fluoro-4'-methoxyphenyl)methyl]-1'-isopropyl-5'-methyl-1H-pyrazole-3'-O-(2,3,4,6-tetrabenzyl)-β-D-glucopyranoside 2.2 g (2.9 mmol) of 4'-[(3'-fluoro-4'-methoxyphenyl)methyl]-5'-methyl-1H-pyrazole-3'-O-(2,3,4,6-tetrabenzyl)-β-D-glucopyranoside was dissolved in 44 ml of dimethylformamide. 9.6 g (29.5 mmol) of cesium carbonate and 2.5 g (14.8 mmol) of isopropyl iodide were added thereto and the mixture was stirred at room temperature overnight.

200 ml of water, 50 ml of saturated aqueous sodium chloride solution and 300 ml of dichloromethane were added and the organic layer was extracted, dried over anhydrous sodium sulfate and concentrated. The product was purified by silica gel column chromatography (hexane~ethyl acetate: hexane=1:3) and concentrated under reduced pressure to obtain 1.7 g (2.2 mmol) of the intended product (yield 74%).

¹H-NMR (300 MHz, CDCl₃) δ: 7.12-7.32 (20H, m), 6.80-6.92 (2H, m), 6.68 (1H, t, J=8.4), 5.47 (1H, d, J=7.2), 4.74-4.94 (5H, m), 4.44-4.64 (5H, m), 4.24-4.32 (1H, m), 3.73 (3H, s), 3.60-3.72 (6H, m), 2.06 (3H, s), 1.38 (3H, t, J=7.5). ESI-MS(m/z): 801[(M+H)⁺].

Process 5

Synthesis of 4-[(3-fluoro-4-methoxyphenyl)methyl]-1-isopropyl-5-methyl-1H-pyrazole-3-O-β-D-glucopyranoside 1.7 g (2.2 mmol) of 4'-[(3'-fluoro-4'-methoxyphenyl)methyl]-1'-isopropyl-5'-methyl-1H-pyrazole-3'-O-(2,3,4,6-tetrabenzyl)-β-D-glucopyranoside was dissolved in 70 ml of ethanol. 1.0 g of 20% palladium hydroxide-carbon was added thereto and the mixture was stirred for 2 hours under hydrogen atmosphere. The reaction mixture was filtrated by a filter cell and the filtrate was concentrated and purified by silica gel chromatography (15% methanol:dichloromethane) and then concentrated under reduced pressure to obtain 828 mg (1.9 mmol) of the intended product (yield 88%).

¹H-NMR (300 MHz, DMSO-d6) δ: 6.92-7.04 (3H, m), 5.20 (1H, d, J=4.5), 5.11 (1H, d, J=7.2), 5.02 (1H, d, J=3.6), 4.93 (1H, d, J=4.5), 4.41 (1H, t, J=5.7), 4.28-4.40 (1H, m), 3.77 (3H, s), 3.56-3.66 (1H, m), 3.42-3.52 (1H, m), 3.08-3.24 (4H, m), 2.07 (3H, s), 1.24-1.30 (3H, m). ESI-MS(m/z): [441(M+H)⁺].

Example 10

Synthesis of 4'-[(3'-fluoro-4'-methoxyphenyl)methyl]-1'-isopropyl-5'-methyl-1H-pyrazole-3'-O-(6-carbomethoxy)-β-D-glucopyranoside 820 mg (1.9 mmol) of 4-[(3-fluoro-4-methoxyphenyl)methyl]-1-isopropyl-5-methyl-1H-pyrazole-3-O-β-D-glucopyranoside was dissolved in 8 ml of collidine and cooled down to 0° C. 10 minutes later, 0.22 ml of methyl chlorocarbonate was added thereto and the mixture was stirred for 7 hours, neutralized with 2N HCl and extracted with ethyl acetate. Then the organic layer was dried over anhydrous sodium sulfate, concentrated and purified by silica gel chromatography (ethyl acetate) and then concentrated under reduced pressure to obtain 303 mg (0.61 mmol) of the intended product (yield 33%).

¹H-NMR (300 MHz, CDCl₃) δ: 6.80-6.92 (3H, m), 5.02 (1H, d, J=8.1), 4.40 (2H, s), 4.22-4.34 (1H, m), 3.85 (3H, s), 3.78 (3H, s), 3.44-3.66 (6H, m), 2.08 (3H, s), 1.38 (6H, d, J=6.6). ESI-MS(m/z): [499(M+H)⁺].

Example 11

Synthesis of 4-[(2-fluoro-4-methoxyphenyl)methyl]-1-isopropyl-5-methyl-1H-pyrazole-3-O-β-D-glucopyranoside Process 1

Synthesis of ethyl 2-[(2-fluoro-4-methoxy)benzyl]-3-oxobutyrate 3.4 g (12.7 mmol) of the intended product was obtained (yield 65%) from 3.0 g of 2-fluoro-4-methoxybenzaldehyde in the same manner as shown in Process 1 of Example 9.

¹H-NMR (300 MHz, CDCl₃) δ: 7.07 (1H, t, J=8.7), 6.40-6.62 (2H, m), 4.10-4.20 (2H, m), 3.79 (1H, t, J=7.8), 3.77 (3H, s), 3.04-3.18 (2H, m), 2.21 (3H, s), 1.21 (3H, t, J=7.2).

Process 2

Synthesis of 1,2-dihydro-4-[(2-fluoro-4-methoxylphenyl)methyl]-5-methyl-3H-pyrazole-3-one 2.46 g (10.4 mmol) of the intended product was obtained (yield 83%) from 3.4 g of ethyl 2-[(2-fluoro-4-methoxy)benzyl]-3-oxobutyrate in the same manner as shown in Process 2 of Example 9.

¹H-NMR (300 MHz, CDCl₃) δ: 7.02 (1H, t, J=8.7), 6.72 (1H, dd, J=2.4, 12.0), 6.66 (1H, d, J=2.7, 8.4), 3.71 (3H, s), 3.47 (2H, s), 1.99 (3H, s) ESI-MS(m/z): 237[(M+H)⁺], 235[(M−H)⁻].

Process 3

Synthesis of 4'-[(2'-fluoro-4'-methoxyphenyl)methyl]-5'-methyl-1H-pyrazole-3'-O-(2,3,4,6-tetrabenzyl)-β-D-glucopyranoside 2.6 g (3.46 mmol) of the intended product was obtained (yield 82%) from 1.0 g (4.2 mmol) of 1,2-dihydro-4-[(2-fluoro-4-methoxyphenyl)methyl]-5-methyl-3H-pyrazole-3-one in the same manner as shown in Process 3 of Example 9.

¹H-NMR (300 MHz, DMSO-d6) δ: 7.12-7.32 (20H, m), 6.99 (1H, t, J=9.0), 6.50 (1H, dd, J=2.4, 11.7), 6.42 (1H, dd, J=2.7, 8.4), 5.54 (1H, d, J=7.2), 4.44-4.92 (8H, m), 3.60-3.76 (8H, m), 3.62 (3H, s), 2.09 (3H, s) ESI-MS(m/z): 759[(M+H)⁺], 757[(M−H)⁻].

Process 4

Synthesis of 4'-[(2'-fluoro-4'-methoxyphenyl)methyl]-1'-isopropyl-5'-methyl-1H-pyrazole-3'-O-(2,3,4,6-tetrabenzyl)-β-D-glucopyranoside 157 mg (0.19 mmol) of the intended product was obtained (yield 70%) from 212 mg (0.28 mmol) of 4'-[(2'-fluoro-4'-methoxyphenyl)methyl]-5'-methyl-1H-pyrazole-3'-O-(2,3,4,6-tetrabenzyl)-β-D-glucopyranoside in the same manner as shown in Process 4 of Example 9.

¹H-NMR (300 MHz, CDCl₃) δ: 7.14-7.30 (20H, m), 6.99 (1H, t, J=8.7), 6.49 (1H, dd, J=2.4, 11.7), 6.41 (1H, dd, J=2.4, 8.7), 5.50 (1H, d, J=7.5), 4.74-4.96 (5H, m), 4.46-

4.66 (5H, m), 4.22-4.32 (1H, m), 3.64(3H, s), 3.60-3.74 (6H, m), 2.08 (3H, s), 1.37 (6H, t, J=6.6). ESI-MS(m/z): 801 [(M+H)$^+$].

Process 5

Synthesis of 4-[(2-fluoro-4-methoxyphenyl)methyl]-1-isopropyl-5'-methyl-1H-pyrazole-3-O-β-D-glucopyranoside 80 mg (0.18 mmol) of the intended product was obtained (yield 97%) from 150 mg (0.19 mmol) of 4'-[(2'-fluoro-4'-methoxyphenyl)methyl]-1'-isopropyl-5'-methyl-1H-pyrazole-3'-O-(2,3,4,6-tetrabenzyl)-β-D-glucopyranoside in the same manner as shown in Process 5 of Example 9.

$^1$H-NMR (300 MHz, DMSO-d6) δ: 7.09 (1H, t, J=9.0), 6.73 (1H, dd, J=2.7, 12.3), 6.66 (1H, dd, J=2.7, 8.7), 5.18 (1H, d, J=4.8), 5.11 (1H, d, J=7.5), 5.01 (1H, d, J=4.2), 4.91 (1H, d, J=4.2), 4.42 (1H, t, J=6.0), 4.30-4.38 (1H, m), 3.72 (3H, s), 3.53 (2H, s), 3.42-3.66 (2H, m), 3.06-3.24 (4H, m), 2.07 (3H, s), 1.28 (3H, d, J=2.7), 1.26 (3H, d, J=2.7). ESI-MS(m/z): 441[(M+H)$^+$], 439[(M–H)$^-$].

Example 12

Synthesis of 4'-[(2'-fluoro-4'-methoxyphenyl)methyl]-1'-isopropyl-5'-methyl-1H-pyrazole-3'-O-(6-carbomethoxy)-β-D-glucopyranoside 380 mg (0.76 mmol) of the intended product was obtained (yield 31%) from 1.1 g (2.42 mmol) of 4-[(2-fluoro-4-methoxyphenyl)methyl]-1-isopropyl-5'-methyl-1H-pyrazole-3-O-β-D-glucopyranoside.

$^1$H-NMR (300 MHz, CDCl$_3$) δ: 7.08 (1H, t, J=8.4), 6.52-6.62 (2H, m), 5.02 (1H, d, J=7.8), 4.64 (1H, brs), 4.40 (2H, d, J=2.4), 4.24-4.33 (1H, m), 3.77 (3H, s), 3.75 (3H, s), 3.59 (3H, s), 3.10-3.66 (6H, m), 1.38 (3H, s), 1.35 (3H, s)

Example 13

Synthesis of 4-[(3-fluoro-4-methylphenyl)methyl]-1-isopropyl-5-methyl-1H-pyrazole-3-O-β-D-glucopyranoside Process 1

Synthesis of ethyl 2-[(3-fluoro-4-methyl)benzyl]-3-oxobutyrate 4.5 g (17.9 mmol) of the intended product was obtained (yield 82%) from 3.0 g (21.7 mmol) of 3-fluoro-4-methylbenzaldehyde in the same manner as shown in Process 1 of Example 9.

$^1$H-NMR (300 MHz, CDCl$_3$) δ: 7.06 (1H, t, J=8.1), 6.78-6.88 (2H, m), 4.15 (2H, q, J=6.9), 3.73 (1H, t, J=7.8), 3.10 (1H, d, J=7.8), 2.22 (3H, s), 2.19 (3H, s), 1.22 (3H, t, J=6.9).

Process 2

Synthesis of 1,2-dihydro-4-[(3-fluoro-4-methylphenyl)methyl]-5-methyl-3H-pyrazole-3-one 2.3 g (10.5 mmol) of the intended product was obtained (yield 93%) from 2.84 g (11.3 mmol) of ethyl 2-[(3-fluoro-4-methyl)benzyl]-3-oxobutyrate in the same manner as shown in Process 2 of Example 9.

$^1$H-NMR (300 MHz, DMSO-d6) δ: 7.11 (1H, d, J=8.4), 6.81-6.89 (2H, m), 3.49 (2H, s), 2.13 (3H, s), 1.98 (3H, s). ESI-MS(m/z): 221[(M+H)$^+$]

Process 3

Synthesis of 4'-[(3'-fluoro-4'-methylphenyl)methyl]-5'-methyl-1H-pyrazole-3'-O-(2,3,4,6-tetraacetyl)-β-D-glucopyranoside 2.1 g (5.0 mmol) of 2,3,4,6-O-tetraacetyl-α-D-glucopyranosyl bromide, 1.1 g (5.0 mmol) of 1,2-dihydro-4-[(3-fluoro-4-methylphenyl)methyl]-5-methyl-3H-pyrazole-3-one and 1.38 g (5 mmol) of silver carbonate were dissolved in 50 ml of dried THF (not containing stabilizer) and the mixture was stirred under dark at 65° C. overnight. The reaction mixture was filtrated with a filter cell and dichloromethane was added thereto. After washing the mixture with water, the organic layer was dried over anhydrous sodium sulfate, concentrated and purified by silica gel chromatography (hexane~ethyl acetate:hexane=1:3) and then concentrated under reduced pressure to obtain 1.1 g (2.0 mmol) of the intended product (yield 40%).

$^1$H-NMR (300 MHz, CDCl$_3$) δ: 7.03 (1H, t, J=7.5), 6.82 (1H, dd, J=1.2, 7.8), 6.74 (1H, dd, J=1.5, 10.8), 5.59 (1H, d, J=8.1), 5.16-5.30 (3H, m), 4.31 (1H, dd, J=3.9, 12.3), 4.12 (1H, dd, J=2.1, 12.3), 3.82-3.88 (1H, m), 3.63 (1H, d, J=15.9), 3.54 (1H, d, J=15.9), 2.20 (3H, d, J=1.5), 2.11(3H, s), 2.06 (3H, s), 2.03 (3H, s), 2.02 (3H, s), 1.91 (3H, s). ESI-MS(m/z): 551[(M+H)$^+$], 549[(M–H)$^-$].

Process 4

Synthesis of 4'-[(3'-fluoro-4'-methylphenyl)methyl]-1'-isopropyl-5'-methyl-1H-pyrazole-3'-O-(2,3,4,6-tetraacetyl)-β-D-glucopyranoside 290 mg (0.53 mmol) of 4'-[(3'-fluoro-4'-methylphenyl)methyl]-5'-methyl-1H-pyrazole-3'-O-(2,3,4,6-tetraacetyl)-β-D-glucopyranoside was dissolved in 6 ml of dimethylformaldehyde. 1.7 g (5.2 mmol) of cesium carbonate and 447 mg (2.6 mmol) of isopropyl iodide were added thereto and the mixture was stirred at room temperature over night. After adding water, saturated aqueous sodium chloride solution and dichloromethane, the organic layer was extracted by a separating funnel, dried over anhydrous sodium sulfate and concentrated. The product was purified by silica gel chromatography (hexane~ethyl acetate:hexane=1:3) and then concentrated under reduced pressure to obtain 165 mg (0.28 mmol) of the intended product (yield 53%).

$^1$H-NMR (300 MHz, CDCl$_3$) δ: 7.02 (1H, t, J=7.8), 6.82 (1H, d, J=7.8), 6.74 (1H, d, J=10.8), 5.79 (1H, d, J=8.1), 5.12-5.34 (3H, m), 4.18-4.32 (2H, m), 4.06-4.16 (1H, m), 3.78-3.88 (1H, m), 3.48-3.64 (2H, m), 2.19 (3H, s), 2.07 (3H, s), 2.06 (3H, s), 2.04 (3H, s), 2.02 (3H, s), 1.93 (3H, s). ESI-MS(m/z): 593[M$^+$].

Process 5

Synthesis of 4-[(3-fluoro-4-methylphenyl)methyl]-1-isopropyl-5-methyl-1H-pyrazole-3-O-β-D-glucopyranoside 56 mg (0.09 mmol) of 4'-[(3'-fluoro-4'-methylphenyl)methyl]-1'-isopropyl-5'-methyl-1H-pyrazole-3'-O-(2,3,4,6-tetraacetyl)-β-D-glucopyranoside was dissolved in 0.2 ml of methanol and 0.4 ml of tetrahydrofuran. 0.38 ml of 1N LiOH was added at 0° C. thereto and the mixture was stirred for 1 hour. After adding water and ethyl acetate, the organic layer was extracted, dried, concentrated and purified by silica gel chromatography (15% methanol:dichloromethane) and then concentrated under reduced pressure to obtain 34 mg (0.08 mmol) of the intended product (yield 85%).

$^1$H-NMR (300 MHz, DMSO-d6) δ: 7.11 (1H, t, J=8.4), 5.19 (1H, d, J=4.8), 5.09 (1H, d, J=7.5), 4.99 (1H, d, J=3.9), 4.91 (1H, d, J=4.2), 4.41 (1H, t, J=5.7), 4.28-4.38 (1H, m), 3.56 (2H, m), 3.54-3.64 (1H, m), 3.40-3.50 (1H, m), 3.06-3.24 (4H, m), 2.13 (3H, s), 2.05 (3H, s), 1.26 (3H, d, J=3.0), 1.24 (3H, d, J=3.0). ESI-MS(m/z): 425[(M+H)$^+$], 423[(M−H)$^-$].

Example 14

Synthesis of 4'-[(3'-fluoro-4'-methylphenyl)methyl]-1'-isopropyl-5'-methyl-1H-pyrazole-3'-O-(6-carbomethoxy)-β-D-glucopyranoside 283 mg (0.59 mmol) of the intended product was obtained (yield 75%) from 334 mg (0.787 mmol) of 4-[(3-fluoro-4-methylphenyl)methyl]-1-isopropyl-5-methyl-1H-pyrazole-3-O-β-D-glucopyranoside in the same manner as shown in Example 12.

$^1$H-NMR (300 MHz, DMSO-d6) δ: 1.26(3H, d, J=6.3 Hz), 1.28(3H, d, J=6.3 Hz), 2.07(3H, s), 2.15(3H, s), 3.09-3.41(4H, m), 3.56(2H, s), 4.10(1H, dd, J=6.0, 11.4 Hz), 4.29(1H, dd, J=1.8, 11.7 Hz), 4.34(1H, m), 5.10(1H, d, J=7.8 Hz), 5.13(1H, d, J=5.1 Hz), 5.24(1H, d, J=5.1 Hz), 5.31(1H, d, J=5.1 Hz), 6.89-7.13(3H, m). ESI-MS(m/z): 483[M+H]$^+$ 481[(M−H)$^-$]

Example 15

Synthesis of 4-[(4-ethylphenyl)methyl]-1-isopropyl-5-methyl-1H-pyrazole-3-O-β-D-glucopyranoside

Process 1

Synthesis of ethyl 2-(4-ethylbenzyl)-3-oxobutyrate 3.9 g (35.7 mmol) of the intended product was obtained (yield 70%) from 3.0 g of 4-ethylbenzaldehyde in the same manner as shown in Process 1 of Example 9.

$^1$H-NMR (300 MHz, CDCl$_3$) δ: 4.15 (2H, q, J=7.2), 3.76 (1H, t, J=7.5), 3.12 (2H, d, J=8.1), 2.60 (2H, q, J=7.8), 2.19 (3H, s), 1.21 (6H, t, J=7.2)

Process 2

Synthesis of 1,2-dihydro-4-[(4-ethylphenyl)methyl]-5-methyl-3H-pyrazole-3-one 3.1 g (14.3 mmol) of the intended product was obtained (yield 91%) from 3.9 g of ethyl 2-(4-ethylbenzyl)-3-oxobutyrate in the same manner as shown in Process 2 of Example 9.

$^1$H-NMR (300 MHz, DMSO-d6) δ: 7.06 (4H, s), 3.49 (2H, s), 2.52 (2H, q, J=7.8), 1.99 (3H, s), 1.33 (3H, t, J=7.5) ESI-MS(m/z): 217[(M+H)$^+$], 215[(M−H)$^-$].

Process 3

Synthesis of 4'-[(4-ethylphenyl)methyl]-5'-methyl-1H-pyrazole-3'-O-(2,3,4,6-tetrabenzyl)-β-D-glucopyranoside 2.3 g (3.1 mmol) of the intended product was obtained (yield 62%) from 1.0 g (4.6 mmol) of 1,2-dihydro-4-[(4-ethylphenyl)methyl]-5-methyl-3H-pyrazole-3-one in the same manner as shown in Process 3 of Example 9.

$^1$H-NMR (300 MHz, CDCl$_3$) δ: 7.10-7.34 (20H, m), 7.07 (2H, d, J=8.4), 6.97 (2H, d, J=8.4), 5.23 (1H, d, J=6.9), 4.44-5.00 (8H, m), 3.56-3.80 (8H, m), 2.50 (2H, q, J=7.5), 2.08 (3H, s), 1.13 (3H, t, J=7.5): ESI-MS(m/z): 739[(M+H)$^+$], 737[(M−H)$^-$].

Process 4

Synthesis of 4'-[(4-ethylphenyl)methyl]-1'-isopropyl-5'-methyl-1H-pyrazole-3'-O-(2,3,4,6-tetrabenzyl)-β-D-glucopyranoside 1.6 g (2.0 mmol) of the intended product was obtained (yield 79%) from 1.9 g (2.6 mmol) of 4'-[(4-ethylphenyl)methyl]-5'-methyl-1H-pyrazole-3'-O-(2,3,4,6-tetrabenzyl)-β-D-glucopyranoside in the same manner as shown in Process 4 of Example 9.

$^1$H-NMR (300 MHz, CDCl$_3$) δ: 7.14-7.38 (20H, m), 7.07 (2H, d, J=8.1), 6.97 (2H, d, J=8.1), 5.47 (1H, d, J=7.5), 4.20-5.00 (9H, m), 3.60-3.76 (8H, m), 2.52 (2H, q, J=7.8), 2.07 (3H, s), 1.37 (6H, t, J=6.9), 1.14 (3H, t, J=8.1): 781[(M+H)$^+$].

Process 5

Synthesis of 4-[(4-ethylphenyl)methyl]-1-isopropyl-5'-methyl-1H-pyrazole-3-O-β-D-glucopyranoside 743 mg (1.8 mmol) of the intended product was obtained (yield 87%) from 1.6 g (2.0 mmol) of 4'-[(4-ethylphenyl)methyl]-1'-isopropyl-5'-methyl-1H-pyrazole-3'-O-(2,3,4,6-tetrabenzyl)-β-D-glucopyranoside in the same manner as shown in Process 5 of Example 9.

$^1$H-NMR (300 MHz, DMSO-d6) δ: 7.09 (2H, d, J-7.8), 7.03 (2H, d, J=7.8), 5.18 (1H, brd, J=4.5), 5.11 (1H, d, J=6.9), 4.84-5.02 (2H, m), 4.26-4.44 (3H, m), 3.40-3.64 (3H, m), 3.04-3.26 (4H, m), 2.51 (2H, q, J=7.5), 2.06 (3H, s), 1.25 (6H, d, J=6.6), 1.14 (3H, t, J=5.7): 421[(M+H)$^+$], 419[(M−H)$^-$].

Example 16

Synthesis of 4'-[(4-ethylphenyl)methyl]-1'-isopropyl-5'-methyl-1H-pyrazole-3'-O-(6-carbomethoxy)-β-D-glucopyranoside 570 mg (1.2 mmol) of the intended product was obtained (yield 71%) from 702 mg (1.67 mmol) of 4-[(4-ethylphenyl)methyl]-1'-isopropyl-5'-methyl-1H-pyrazole-3-O-β-D-glucopyranoside in the same manner as shown in Example 10.

$^1$H-NMR (300 MHz, CDCl$_3$) δ: 7.08 (4H, s), 4.99 (1H, d, J=7.5), 4.24-4.48 (4H, m), 3.77 (3H, s), 3.44-3.68 (6H, m), 2.94-3.16 (2H, m), 2.58 (2H, q, J=7.8), 2.09 (3H, s), 1.36 (6H, d, J=6.6), 1.20 (3H, t, J=7.8) ESI-MS(m/z): 479[(M+H)$^+$], 477[(M−H)$^-$].

Referential Example 1(Example 35 of WO01/16147)

Synthesis of 4-[(4-isopropoxyphenyl)methyl]-5-methyl-1H-pyrazole-3-O-β-D-glucopyranoside The product was synthesized in accordance with the methods described in Example 9 (yield point 253 mg).

$^1$H-NMR (300 MHz, DMSO-d6) δ: 7.07 (1H, d, J=8.4), 6.75 (1H, d, J=8.4), 5.12-5.20 (2H, m), 5.00 (1H, d, J=3.9), 4.92 (1H, d, J=3.9), 4.42-4.56 (2H, m), 3.58-3.68 (1H, m), 3.51 (2H, s), 3.42-3.54 (1H, m), 3.06-3.24 (4H, m), 2.00 (3H, s), 1.22 (6H, d, J=6.3) ESI-MS(m/z): 409[(M+H)$^+$], 407[(M−H)$^-$].

The structures of the compounds shown in Example 1 to 16 and Referential Example 1 are described as follows:

Example Compound 1
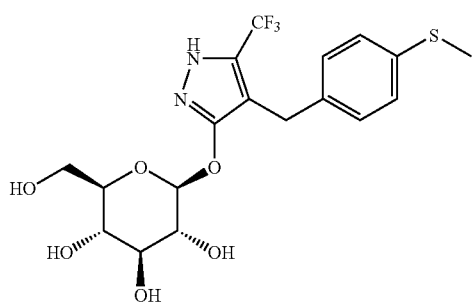
Example Compound 2
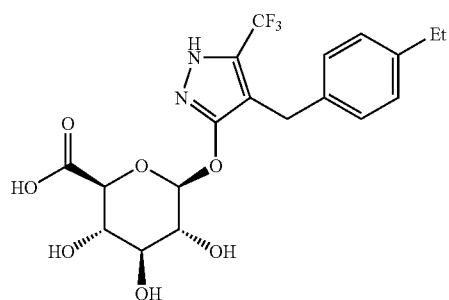
Example Compound 3
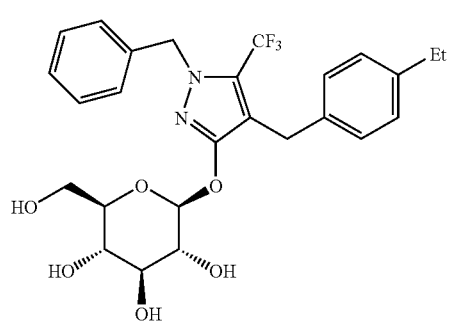
Example Compound 4
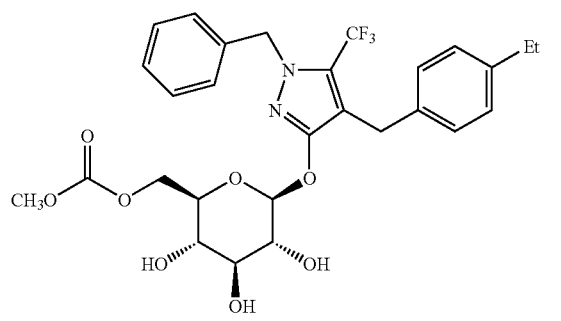
Example Compound 5
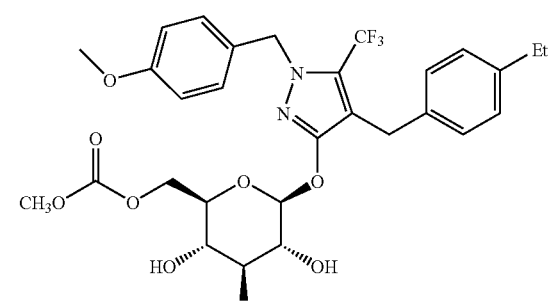
Example Compound 6
Example Compound 7
Example Compound 8
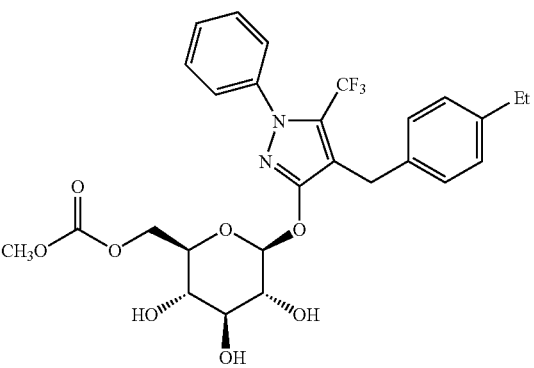

Example Compound 9
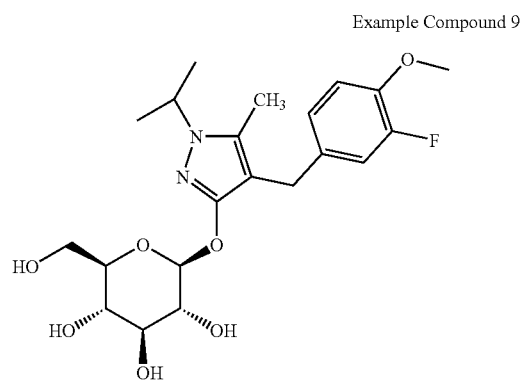
Example Compound 10
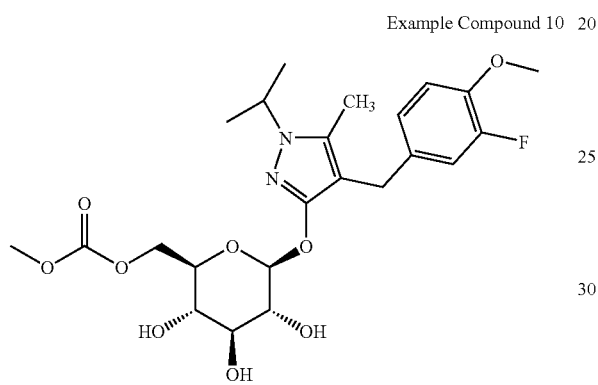
Example Compound 11
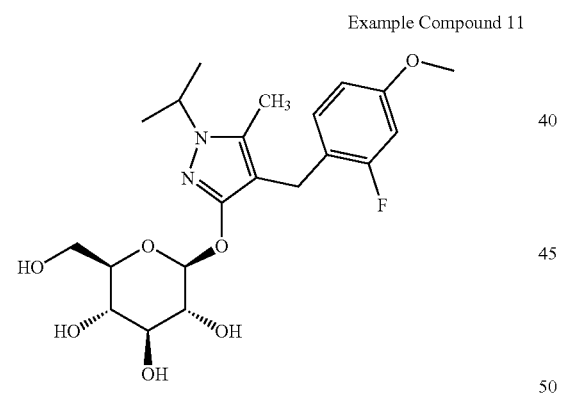
Example Compound 12
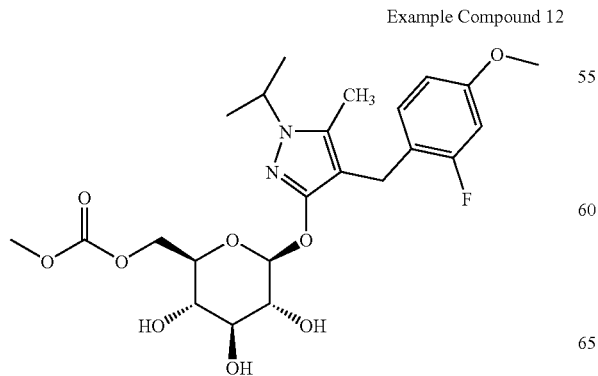
Example Compound 13
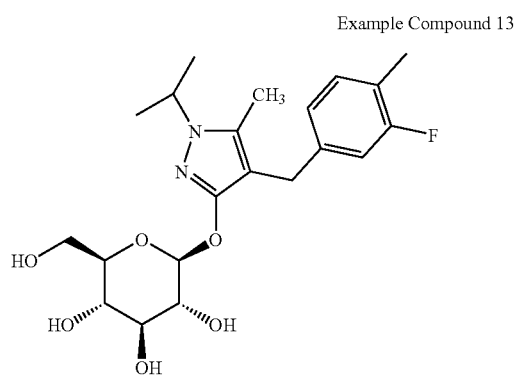
Example Compound 14
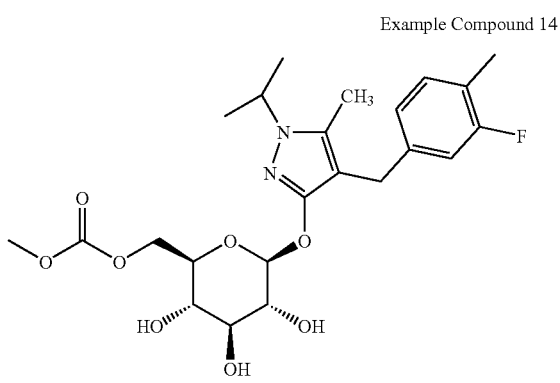
Example Compound 15
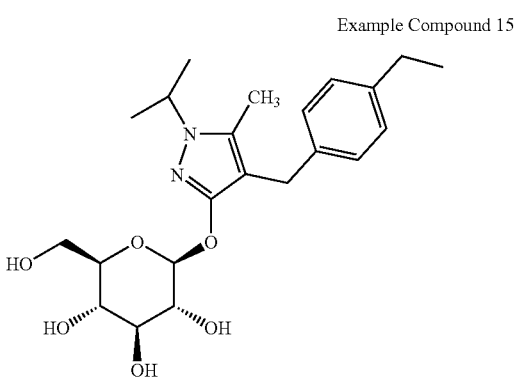
Example Compound 16
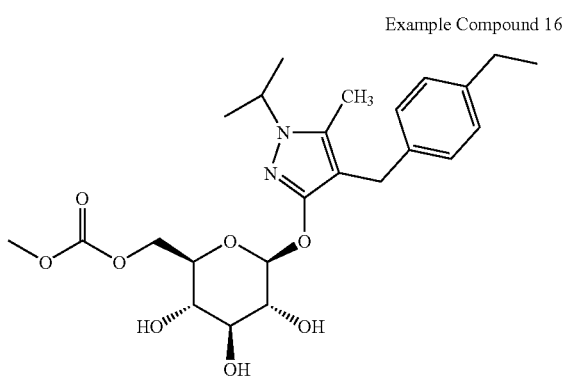

-continued

Referential Example Compound 1

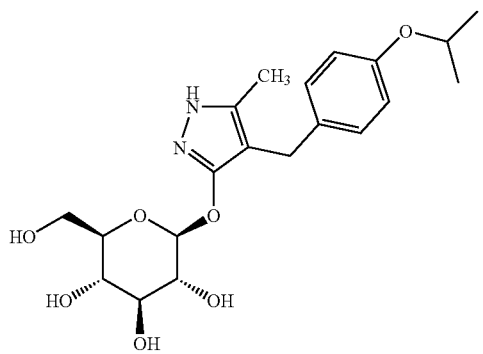

Example 17

Evaluation of Inhibiting Activity on Renal Brush Border Membrane Glucose Uptake

The test compound was dissolved in 100 mM Mannitol-10 mM HEPES/Tris (pH 7.4) and solutions having various concentrations were prepared.

Renal brush border membrane was prepared from a rat kidney and the solutions of the test compounds were added thereto and the product was incubated at 37° C. for 30 minutes. Then $^{14}$C-D-glucose was added and the mixture was incubated for 1 minute. After tie reaction of glucose uptake was stopped by a solution containing 1 mM of phloridzin, the activity of $^{14}$C-D-glucose on $^{14}$C was measured by a liquid scintillation counter. The intensity of inhibition was calculated by subtracting the amount of taken glucose that is independent on sodium from the amount of taken glucose of the object samples. The results of the evaluation are shown in Table 1.

TABLE 1

| The test compounds | Inhibition intensity (concentration of the test compounds) |
| --- | --- |
| Example Compound 1 | 84% (10 μM) |
| Example Compound 2 | 30% (100 μM) |

Example 18

Evaluation of Activity on Rat's Sugar Urine Excretion 5-week old male Wistar rats (purchased from Charles River Japan, Inc.) were used in the experiment after they were housed in a metabolic cage for about one week in advance. The test compounds were suspended in olive oil and 20 mg/ml solution was prepared so that the dosage given per 1 kg of the weight of the rats was 5 ml.

After the rats were not fed for 4 hours, the test compounds were orally administered to them at 11 a.m. Their urine was collected, from that taken just after the administration to that taken 24 hours after the administration and its volume was measured. Then, the concentration of glucose in urine was measured by glucose oxidase method and urinary glucose excreted per a day and an individual was calculated. The results are shown in Table 2.

TABLE 2

| | The dosage | The amount of excreted glucose in urine (mg) |
| --- | --- | --- |
| Example Compound 4 | 100 mg/kg | 27 |
| Example Compound 6 | 100 mg/kg | 59 |
| Example Compound 8 | 100 mg/kg | 4.1 |
| Example Compound 10 | 100 mg/kg | 734 |
| Example Compound 14 | 100 mg/kg | 918 |
| Example Compound 16 | 100 mg/kg | 598 |
| | 30 mg/kg | 294 |
| | 10 mg/kg | 263 |
| | 3 mg/kg | 28 |
| Referential Example Compound 1 | 100 mg/kg | 14 |

It is obvious from the results shown above that the new pyrazole derivatives have higher inhibiting activity on glucose uptake and activity on urinary glucose excretion.

Especially, the inventors have found that the compounds wherein the substituents of hydroxyl group of glucopyranosyl group are lower alkoxycarbonyl group such as methoxy carbonyl group act as, so-called, a prodrug and the compounds in the present invention have high activity on urinary glucose excretion when they are orally administered.

The inventors also have found that the compounds wherein any one of R1, R2, R4, or R5 of general formula (1A) has a fluorine atom have particularly high activity on urinary glucose excretion. It is obvious from Example 10 and Example 14.

Further, they have found that the compound of Example 16 has particularly high activity on urinary glucose excretion. Example compound 16, which has high activity on urinary glucose excretion, still has high activity when the compound is orally administered in lower doses such as 30 mg/kg or lower. The intended compound is not specifically described in WO01/16147.

Besides, Table 2 shows that the compounds of the present invention such as example compounds 10, 14 and 16 have much higher activity on urinary glucose excretion, as compared to Example 35 of WO01/16147 (Referential Example 1 of the present specification).

Namely, new pyrazole derivatives of the present invention show outstanding antidiabetic activity and, therefore, they are highly useful in the pharmaceutical industry.

What is claimed is:

1. A pyrazole compound of formula (1A) or (1B) or a pharmaceutically acceptable salt thereof:

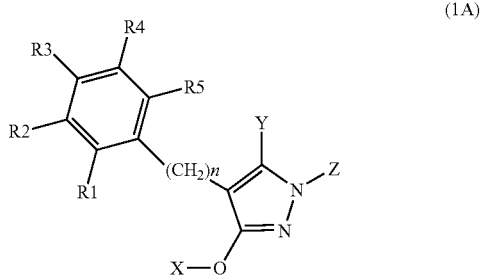

(1A)

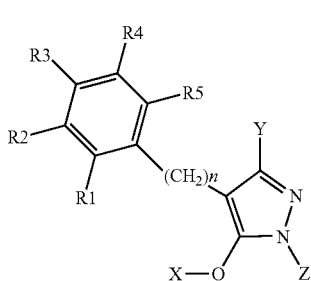

(1B)

wherein X represents a hydrogen atom; Y represents a lower alkyl group or a perfluoro lower alkyl group; Z represents a hydrogen atom, a lower alkyl group, a perfluoro lower alkyl group, an aralkyl group or a phenyl group; R1, R2, R3, R4, and R5 may be the same or different and each represents a hydrogen atom, a lower alkyl group, a perfluoro lower alkyl group, a lower alkoxy group, a perfluoro lower alkoxy group, a lower alkylthio group, a perfluoro lower alkylthio group, a lower alkyl amino group, a halogeno atom, a lower alkanoyl group, a lower alkenyl group or a lower alkynyl group, and n represents an integer from 0 to 3, wherein at least two of R1, R2, R3, R4, and R5 independently represents a lower alkyl group, a perfluoro lower alkyl group, a lower alkoxy group, a perfluoro lower alkoxy group, a lower alkylthio group, a perfluoro lower alkylthio group, a lower alkyl amino group, a halogeno atom, a lower alkanoyl group, a lower alkenyl group or a lower alkynyl group.

2. The pyrazole compound or pharmaceutically acceptable salt thereof of claim 1, wherein n=1.

3. The pyrazole compound or pharmaceutically acceptable salt thereof of claim 1, wherein Z is a hydrogen atom or a lower alkyl group, and n=1.

4. The pyrazole compound or pharmaceutically acceptable salt thereof of claim 1, wherein R3 is a lower alkyl group, a lower alkoxy group, a lower alkenyl group, or a lower alkynyl group, at least one of R1, R2, R4, and R5 is a halogen atom, and n=1.

5. The pyrazole compound or pharmaceutically acceptable salt thereof of claim 1, wherein R3 is selected from the group consisting of a methoxy group, a methyl group, an ethyl group, an ethynyl group, and a propynyl group, and n=1.

6. The pyrazole compound or pharmaceutically acceptable salt thereof of claim 1, wherein R2 is a fluorine atom, R1, R4, and R5 are all hydrogen, and n=1.

7. The pyrazole compound or pharmaceutically acceptable salt thereof of claim 1, wherein R1 is a fluorine atom, R2, R4, and R5 are all hydrogen, and n=1.

8. The pyrazole compound or pharmaceutically acceptable salt thereof of claim 1, wherein R3 is a methoxy group, at least one of R1, R2, R4, and R5 is a fluorine atom, and n=1.

9. The pyrazole compound or pharmaceutically acceptable salt thereof of claim 1, wherein R3 is a methoxy group, R2 is a fluorine atom, each of R1, R4, and R5 is a hydrogen atom, Y is a methyl group or a trifluoromethyl group, Z is an isopropyl group or a hydrogen atom, and n=1.

10. The pyrazole compound or pharmaceutically acceptable salt thereof of claim 9, wherein Y is a methyl group and Z is a hydrogen atom.

11. The pyrazole compound or pharmaceutically acceptable salt thereof of claim 1, wherein R3 is a methoxy group, R1 is a fluorine atom, each of R2, R4, and R5 is a hydrogen atom, Y is a methyl group or a trifluoromethyl group, Z is an isopropyl group or a hydrogen atom, and n=1.

12. The pyrazole compound or pharmaceutically acceptable salt thereof of claim 11, wherein Y is a methyl group and Z is a hydrogen atom.

13. The pyrazole compound or pharmaceutically acceptable salt thereof of claim 1, wherein R3 is a methyl group, at least one of R1, R2, R4, and R5 is a fluorine atom, and n=1.

14. The pyrazole compound or pharmaceutically acceptable salt thereof of claim 1, wherein R3 is a methyl group, R2 is a fluorine atom, each of R1, R4, and R5 is a hydrogen atom, Y is a methyl group or a trifluoromethyl group, Z is an isopropyl group or a hydrogen atom, and n=1.

15. The pyrazole compound or pharmaceutically acceptable salt thereof of claim 14, wherein Y is a methyl group and Z is a hydrogen atom.

16. A pyrazole compound of formula (1A) or (1B) or a pharmaceutically acceptable salt thereof:

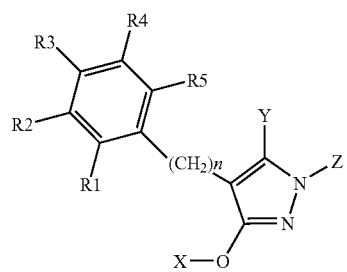

(1A)

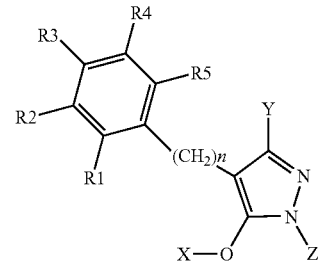

(1B)

wherein X represents a hydrogen atom; Y represents a lower alkyl group or a perfluoro lower alkyl group; Z represents a hydrogen atom, a lower alkyl group, a perfluoro lower alkyl group, an aralkyl group or a phenyl group; R1, R2, R4, and R5 may be the same or different and each represents a hydrogen atom, a lower alkyl group, a perfluoro lower alkyl group, a lower alkoxy group, a perfluoro lower alkoxy group, a lower alkylthio group, a perfluoro lower alkylthio group, a lower alkyl amino group, a halogeno atom, a lower alkanoyl group, a lower alkenyl group or a lower alkynyl group; and n represents an integer from 0 to 3, wherein at least one of R1, R2, R4, and R5 represents a lower alkyl group having 1 to 6 carbon atoms, a lower alkylthio group having 1 to 6 carbon atoms, a halogeno atom, a lower alkoxy group, a lower alkenyl group, or a lower alkynyl group; and R3 represents a lower alkyl group having 1 to 6 carbon atoms, a lower alkylthio group having 1 to 6 carbon atoms, a halogeno atom, a lower alkoxy group, a lower alkenyl group, or a lower alkynyl group.

17. The pyrazole compound or pharmaceutically acceptable salt thereof of claim 16, wherein n=1.

* * * * *